(12) United States Patent
Yang

(10) Patent No.: US 10,226,623 B2
(45) Date of Patent: Mar. 12, 2019

(54) WEARABLE SOAKING PHYSIOTHERAPEUTIC DEVICE WITH INFLATABLE SEAL

(71) Applicant: Jianqiao Yang, Toronto (CA)

(72) Inventor: Jianqiao Yang, Toronto (CA)

( * ) Notice: Subject to any disclaimer, the term of this patent is extended or adjusted under 35 U.S.C. 154(b) by 321 days.

(21) Appl. No.: 15/172,920

(22) Filed: Jun. 3, 2016

(65) Prior Publication Data

US 2017/0050020 A1 Feb. 23, 2017

(30) Foreign Application Priority Data

Aug. 18, 2015 (CN) ...................... 2015 2 0622183 U

(51) Int. Cl.
| | | |
|---|---|---|
| A61N 1/04 | (2006.01) |
| A61N 1/36 | (2006.01) |
| A61M 37/00 | (2006.01) |
| A61H 9/00 | (2006.01) |
| A61F 7/00 | (2006.01) |

(Continued)

(52) U.S. Cl.
CPC ............ *A61N 1/36014* (2013.01); *A61F 7/00* (2013.01); *A61H 9/0078* (2013.01); *A61M 37/00* (2013.01); *A61N 1/0452* (2013.01); *A61N 1/0456* (2013.01); *A61H 23/02* (2013.01); *A61H 35/00* (2013.01); *A61H 2201/0111* (2013.01); *A61H 2201/0207* (2013.01); *A61H 2201/0221* (2013.01); *A61H 2201/0242* (2013.01); *A61H 2201/10* (2013.01); *A61H 2201/1207* (2013.01); *A61H 2201/164* (2013.01); *A61H 2201/165* (2013.01); *A61H 2201/1619* (2013.01); *A61H 2201/1635* (2013.01); *A61H 2201/1654* (2013.01); *A61H 2201/5007* (2013.01); *A61H 2201/5043* (2013.01); *A61H 2201/5048* (2013.01); *A61H 2201/5082* (2013.01); *A61H 2205/06* (2013.01); *A61H 2205/082* (2013.01); *A61H 2205/084* (2013.01); *A61H 2205/10* (2013.01); *A61M 35/00* (2013.01); *A61N 1/322* (2013.01)

(58) Field of Classification Search
CPC .............. A61N 1/36014; A61N 1/0456; A61N 1/0452; A61N 1/044; A61N 1/0448
See application file for complete search history.

(56) References Cited

U.S. PATENT DOCUMENTS

| | | | | |
|---|---|---|---|---|
| 4,583,457 A * | 4/1986 | Volk | .......................... | B41K 3/06 |
| | | | | 101/105 |
| 4,919,148 A * | 4/1990 | Muccio | ................ | A61N 1/0452 |
| | | | | 607/152 |

(Continued)

FOREIGN PATENT DOCUMENTS

| | | |
|---|---|---|
| CN | 1129595 A | 8/1996 |
| CN | 105078643 A | 11/2015 |

*Primary Examiner* — Michael D Abreu

(57) ABSTRACT

A physiotherapeutic device comprises a skin soaker for soaking a portion of the user's skin with a liquid when the device is attached to the user. The soaker comprises a tub for receiving the liquid and a resilient seal at a brim of the tub for sealing engagement with the skin to prevent leak of the liquid. The device also has an electrical stimulator comprising a first electrode and a second electrode for contacting the skin to stimulate tissues under the soaked portion of the skin. The soaked portion of the skin extends between the electrodes and the electrodes are isolated from the liquid.

20 Claims, 28 Drawing Sheets

(51) Int. Cl.
   *A61H 23/02* (2006.01)
   *A61M 35/00* (2006.01)
   *A61N 1/32* (2006.01)
   *A61H 35/00* (2006.01)

(56) References Cited

U.S. PATENT DOCUMENTS

| | | |
|---|---|---|
| 5,156,591 A | 10/1992 | Gross et al. |
| 6,908,448 B2 | 6/2005 | Redding, Jr. |
| 2015/0265825 A1 | 9/2015 | Miller et al. |

\* cited by examiner

WEARABLE SOAKING PHYSIOTHERAPEUTIC DEVICE WITH INFLATABLE SEAL

CROSS-REFERENCE TO RELATED APPLICATIONS

This application claims the benefit of, and priority from, Chinese Utility Model Patent Application No. 201520622183.0, filed Aug. 18, 2015, the entire contents of which are incorporated herein by reference.

FIELD

The present invention relates generally to physiotherapeutic devices, particularly to wearable physiotherapeutic device and related methods and uses.

BACKGROUND

Portable devices for physiotherapy, particularly wearable devices, are useful as they allow the user or patient more freedom and mobility during treatment. For example, the user or patient may move around more freely during treatment, and may conveniently use the device at home, or in hospitals, medical clinics, doctors' offices, or other locations. Portable physiotherapeutic devices include portable electrical stimulation devices, such as massaging devices based on neuromuscular electrical stimulation (NMES) or electromyostimulation, or transcutaneous electrical nerve stimulation (TENS or TNS). Some of such devices may also be called electrical muscle stimulation (EMS) devices. It is also helpful during the physiotherapy treatment to apply heat and a treatment fluid to the skin.

There are known techniques to combine massage treatment with heat or fluid treatment. For example, massaging treatment and heat treatment may be sequentially applied to a patient or a subject. A medicinal substance or solution may also be applied to the skin, before, during, or after a hand massage or heat treatment. However, these techniques typically require visits to, and treatment in, the physician or doctor's office. During such treatments it is inconvenient or difficult for the user or patient to walk around. When a treatment liquid is used to treat the patient's skin, fluid leakage can occur, particularly when the patient moves about. There are also portable devices for combined treatment. For example, CN 10507863 to Ding discloses a portable treatment device with a heated massage head and perforations in the massage head for applying a medicinal solution to the massaged skin surface. However, treatments with such a conventional portable device for physiotherapy are often found to be less effective or less satisfactory, as compared to a combined hand massage and fluid soaking treatment.

Improved portable devices and techniques are still desirable.

SUMMARY

An aspect of the present disclosure relates to a wearable soaking physiotherapeutic device. The device includes an electrical stimulator having an electrode for contacting a part of a user's skin and stimulating tissues under the skin, and includes a soaker for soaking the user' skin adjacent and around the electrode with a treatment fluid. Seals are provided to prevent leakage of the fluid and to isolate the electrode from the treatment fluid during treatment. The soaker has a tub, which when attached to the user's skin can be sealed with the user's skin to form a reservoir for containing a pool of the treatment fluid.

Conveniently, soaking and massaging treatment can be applied simultaneously, which is expected to provide a synergistic treatment effect. Fluid leakage and electric shorting can be prevented even when the user is moving or walking, so the device is convenient to use.

In an aspect, there is disclosed a physiotherapeutic device attachable to a user, comprising a skin soaker for soaking a portion of the user's skin with a liquid when the device is attached to the user, the soaker comprising a tub for receiving the liquid and comprising a resilient seal at a brim of the tub for sealing engagement with the skin to prevent leak of the liquid; and an electrical stimulator comprising a first electrode and a second electrode for contacting the skin to stimulate tissues under the soaked portion of the skin, wherein the soaked portion of the skin extends between the first and second electrodes and the first and second electrodes are isolated from the liquid.

The resilient seal may comprise an inflatable seal. The device may comprise an air pump for inflating the seal and a release valve for deflating the seal. The first electrode may be mounted within the periphery of the soaker, and the soaker may comprise a sealing structure adjacent and around the first electrode for sealing engagement with the skin to isolate the first electrode. Each one of the first and second electrodes may be mounted within the periphery of the soaker. The soaker may be positioned between the first and second electrodes. The electrical stimulator may be configured for neuromuscular electrical stimulation or transcutaneous electrical nerve stimulation. The electrical stimulator may be configured for stimulating the tissues at a pulse frequency of 1 to 300 Hz. The device may comprise a wearable body configured to be worn by the user. The soaker may be formed on the body and the electrical simulator may be mounted on the body. The device may comprise a heater for heating the liquid. The device may comprise coolant tubing extending within the periphery for cooling the liquid. The device may comprise a temperature sensor for sensing a temperature of the liquid and a controller for controlling the heater to regulate the temperature of the liquid. The soaker may comprise a tub for receiving the liquid, and a fluid conduit in communication with the tub for supplying and withdrawing the fluid. The device may comprise a strap for attaching the device to the user. The device may be configured to be attached to the back, a knee, an elbow, or the chest of the user.

In another aspect, there is disclosed a method comprising contacting a subject's skin with first and second electrodes, and applying an electrical signal to the first and second electrodes to stimulate tissues under the skin; and soaking a portion of the skin between the first and second electrodes with a pool of treatment fluid, while isolating the electrodes from contacting the treatment fluid during the soaking. The treatment liquid may be heated. The treatment liquid may comprise a therapeutic agent, such as an alcohol.

Other aspects, features, and embodiments of the present disclosure will become apparent to those of ordinary skill in the art upon review of the following description of specific embodiments in conjunction with the accompanying figures.

BRIEF DESCRIPTION OF THE DRAWINGS

In the figures, which illustrate, by way of example only, embodiments of the present disclosure.

DETAILED DESCRIPTION

Figure 1:
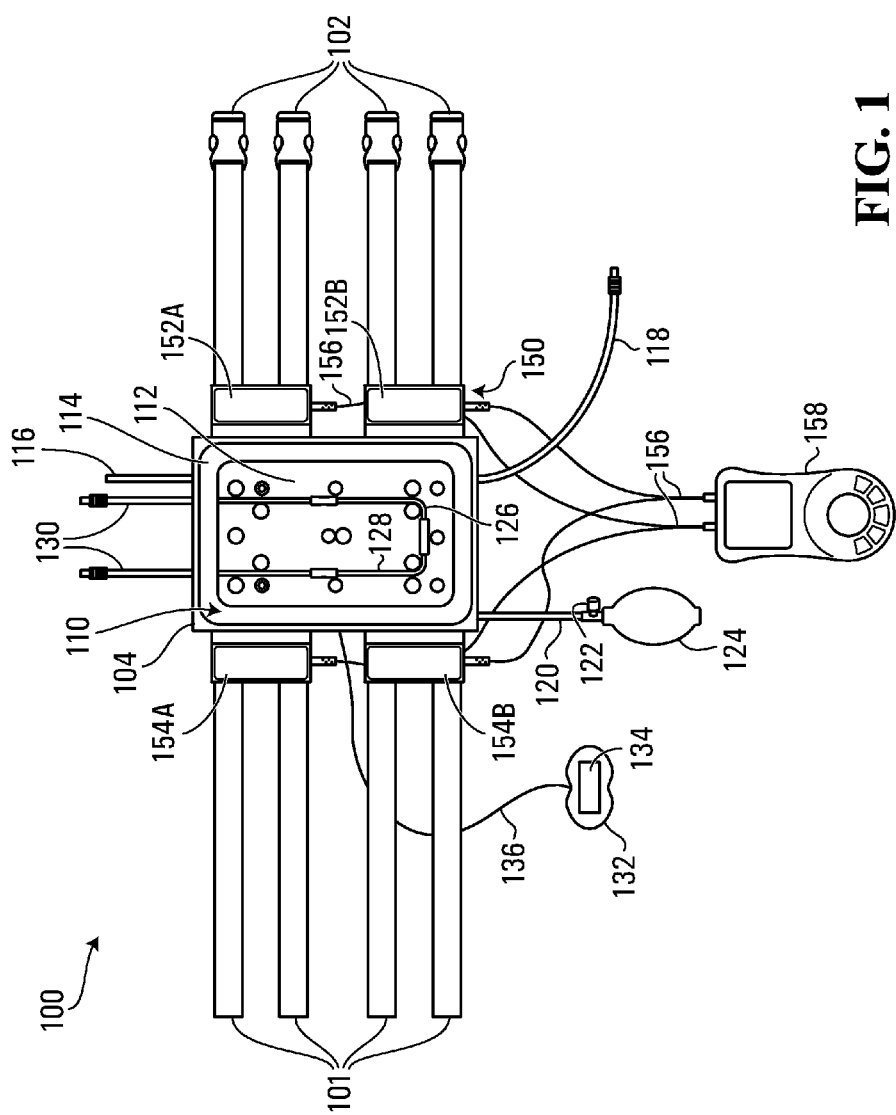
FIG. 1 is a front perspective view of a wearable physiotherapeutic device.

An embodiment of the present disclosure relates to a physiotherapeutic device as illustrated in FIGS. 1 to 8.

As shown in FIGS. 1 to 8, a soaking physiotherapeutic device 100 includes straps 101 and fasteners 102 for attaching device 100 to a user (not shown but see FIG. 9) so device 100 is wearable by the user.

Device 100 may be provided with any suitable fastening mechanisms for attaching device 100 to a user. For example, fasteners 102 may include mating buckles attached to the ends of each strap 101, as depicted in e.g. FIG. 2 and can be understood by those skilled in the art.

Straps or other alternative fastening components may be provided and fixed on the backside of the wearable body for attaching the device to the user during use. For example, elastic bands with or without buckles may be used. Straps with buckles may be more convenient to use. Elastic straps are helpful as it may be easier to prevent leakage of the treatment liquid with elastic straps. With rigid straps, when the user moves around, the tension applied to certain portion of the inflatable seal may be lessened to allow leakage of the liquid. With suitably selected elastic straps, the variation in the applied tension can be less due to compensation of the additional tension produced by stretching a particular strap. The use of buckles allows convenient quick connection and release. The lengths of straps may also be adjustable to accommodate different sizes of different users, and the use at different body parts.

Device 100 includes a soaker 110 and an electrical stimulator 150.

Soaker 110 is configured as a skin soaker for soaking a portion of the user's skin with a liquid when device 100 is attached to the user.

Soaker 110 has a liquid tub 112 formed in a base or support body 104, for receiving a liquid that is to be used to soak the user's skin. Tub 112 has a sufficient depth and volume to form a fluid chamber between the device 100 and the skin of the user when device 100 is worn by the user, and to allow a pool of the liquid to form in the fluid chamber and allow the liquid to flow within the fluid chamber.

With a pool of the liquid in the fluid chamber, when the liquid in the fluid chamber is stimulated, the fluid movement can produce some physical impact on the skin. The volume of the fluid in the tub 112 also has a sufficient heat capacity to allow the temperature of the liquid to be stably controlled. For example, the tub 112 may have a depth of about 2 to 5 mm, or larger.

A resilient seal 114 is provided at the periphery of the tub 112 for sealing engagement with the user's skin to prevent leakage of the liquid, which will be further detailed below.

A fluid inlet tubing 116 and fluid outlet tubing 118 are mounted on soaker 110 for introducing the liquid into the fluid chamber and drain the liquid out of the fluid chamber respectively during use.

Seal 114 is an inflatable seal and has an air conduit 120 connected with a pressure source, such as a hand-held gas pump 124 as illustrated in FIG. 1, through a valve 122. With valve 122 opening, pump 124 may be used to supply pressured air into seal 114 through conduit 120 to inflate seal 114 for sealing the engagement between the user's skin and the soaker 110. Value 122 is closed during treatment for maintaining the air pressure in inflatable seal 114. After use, pressured air may be released from inflatable seal 114 through conduit 120 by opening valve 122.

A heat-exchanger 126 is also provided, which includes heat-exchange tubing 128 and tubing 130 for connecting heat-exchange tubing 128 to a source of a heating or cooling fluid (not shown). The heating or cooling fluid may be water, which can be heated or cooled depending on whether heating or cooling is desired.

As can be appreciated, a separate heating device (not shown) such as an electric heating pad, heating coil, or heating film may also be provided. The heating pad or film may have any suitable size or shape. Typically, the heating film or pad may have a rectangular or circular shape.

During use, the initial temperature of the soaking liquid may be also controlled by heating the soaking liquid before the liquid is introduced into the fluid chamber. In which case, heat-exchanger 126 may be used mainly for cooling purpose.

For example, tubing 128 may be configured to circulate a coolant therethrough for cooling the soaking liquid. Tubing 128 may extend within the tub 112 for a sufficient length for effective cooling.

In different embodiments, various types of fluid conduits may be provided in the soaker 110, such as to allow the treatment or soaking liquid be delivered into the tub 112 during treatment, and be released after treatment. The fluid conduits include inlet conduits and outlet conduits. One or more valves may be provided to control fluid flow. The fluid conduits may be configured and structured in any suitable manner known to those skilled in the art, depending on the shape and size of the base body 104 on which soaker 110 is formed.

For example, the conduits may be built into the base body 104 and may be formed by casting or molding.

One or more ports including fluid input and discharge ports may also be provided, which may be provided with one more valves such as a toggle valve, for supplying and discharging various fluids including the treatment or soaking liquid. The fluid may also include a coolant or air.

Ports may also be provided for connecting tubes and conduits, installing a sensor or detector, or the like.

A temperature sensing device 132 is provided for sensing the temperature of the soaking liquid in the fluid chamber. Temperature sensing device 132 may include a thermocouple (not separately shown) that can be inserted into device 110 for contacting the soaking liquid to measure the temperature of the soaking fluid. Temperature sensing device 132 may also include a circuit (not separately shown) for converting the detected electrical signal to a digital signal or data that can be stored or displayed to the user. Temperature sensing device 132 may include a display 134 for displaying the current temperature. As depicted, the circuit and display 134 is connected to the actual thermocouple sensor by a wire 136. Temperature sensing device 132 may also be connected to a controller (not shown) for controlling the heater 126 to regulate the temperature in the fluid in the fluid chamber.

An electrical stimulator 150 is also provided in device 100. Electrical stimulator 150 includes one or more pairs of electrodes, such as electrode pairs 152A, 154A and electrode pairs 152B, 154B as depicted, for contacting the user's skin to stimulate tissues under the skin. Electrodes 152A and 154A are also individually or collectively referred to as electrode(s) 152, and electrodes 154A and 154B are also individually or collectively referred to as electrode(s) 154 herein.

Each pair of electrodes 152 and 154 are arranged such that, during use, a soaked portion of the user's skin extends between each pair of electrodes 152 and 154, so that at least some tissues under a soaked portion of the skin can be stimulated when an electrical stimulation signal is applied across the electrode pair.

In operation, the electrodes 152 and 154 can be isolated from the soaking liquid in the liquid chamber formed between the user's skin and the tub 110 with the use of the inflatable seal 114, as will be further described below.

In different embodiments, one or more pairs of electrodes may be positioned within the peripheral of soaker 110, such as within tub 112 or within the area enclosed by seal 114. In such a case, a separate sealing seal may be provided to seal each electrode within tub 112 from contacting the soaking liquid. The sealing seal may also be an inflatable seal, which may be connected to a pressure source such as pump 124 through a respective air conduit. The air conduit may be integrated into the base body of device 100, or may be provided by a separate pipe or tube. For example, in a variation of the depicted embodiment in FIG. 1, one or both of the first electrodes 152A, 152B may be replaced with a smaller electrode mounted within the periphery of soaker 110, and a seal including a sealing structure is formed adjacent and around the smaller electrode for sealing engagement with the skin to isolate the electrode 152 from contacting the soaking liquid.

In a further variation, each one of electrodes 152 and 154 may be mounted within the periphery of soaker 110.

Electrical stimulator 150 also includes conductor lines or wires 156 for connecting the electrodes 152, 154 to a control unit 158. The conductor lines 156 and control unit 158 may be provided separately, or may be integrated with the device body 104. In some embodiments, separate commercially available electrical stimulators or massagers may be used, which allow the device 100 to be conveniently adapted for use in different applications. In some cases, the base unit for device 100 and the stimulator 150 may be provided by different vendors separately.

The electrical stimulator 150 may be configured for neuromuscular electrical stimulation or transcutaneous electrical nerve stimulation. The electrical stimulator may be configured for stimulating the tissues at a pulse frequency of 1 to 330 Hz. In some embodiments, the pulse frequency may be from about 2 to 10 Hz. The stimulating frequency may also include a high frequency component modulated by a low (pulse) frequency. The high frequency component may have a frequency of up to about 2 kHz or higher. A typical battery-operated TENS unit is able to modulate pulse width, frequency and intensity. Generally, TENS is applied at high frequency (>50 Hz) with an intensity below motor contraction (sensory intensity) or low frequency (<10 Hz) with an intensity that produces motor contraction.

The stimulation frequency can be modulated, or unmodulated, and may have a high frequency component and a low modulation frequency. The signal profile may be stepped (rectangular or square), triangle, sine, sawtooth, or have any other suitable waveform. For example, waveforms suitable for modulated medium frequency electrotherapy may be used. In a modulated frequency waveform, the high frequency component may be in the range of 2-8 kHz or 2-10 kHz. The lower modulation frequency may be in the range of 1-150 hz. The modulation may be periodic, continuous, cyclic, or varied, and may have different modulation amplitude from 0% to 100%. The waveform may be symmetric or asymmetric.

The electric current or signal strength may be adjustable and may be selected for optimal treatment effect with the user tolerance. For example, in some embodiments, the stimulation current may be in the range of 0.1 to 0.3 mA/cm$^2$. A treatment period may last from a few minutes to 15-20 minutes. A longer treatment period may also be possible or desirable.

As depicted in FIG. 1, device 100 has a base body 104 and soaker 110 is formed on the body 104 and some parts of the electrical simulator 150 are mounted on the body 104.

Operation the soaker 110 and stimulator 150 may be manually controlled or automatically controlled. As alluded to earlier, a controller (not shown) may be provided for controlling the operation of device 100. For example, a heater mounted on device 100 may be controlled with the controller to regulate the temperature of the soaking liquid. The controller may be mounted on the soaker body 104, such as at the back of soaker 110. In different embodiments, the controller may be provided separately. The controller may be in electrical or data communication with the soaker 110 or the stimulator 150 through wire or wireless communication.

In different embodiments, device 100 may be modified and configured for attachment to a different part of the user's body instead of the back. For example, the device may be configured for attachment to an elbow, a knee, a shoulder, or the chest of the user.

In embodiments illustrated herein, each wearable device, such as device 100, is configured to prevent leakage of the soaking liquid, such as the soaking liquid in tub 112 of the soaker 110, with an inflatable seal, such as seal 114. The inflatable seal may be formed of a resilient material with an inner channel, such as channel 140 for receiving a fluid such as air, as better illustrated in FIGS. 2A, 2B, 2C, 2D and 2E.

Figure 2:
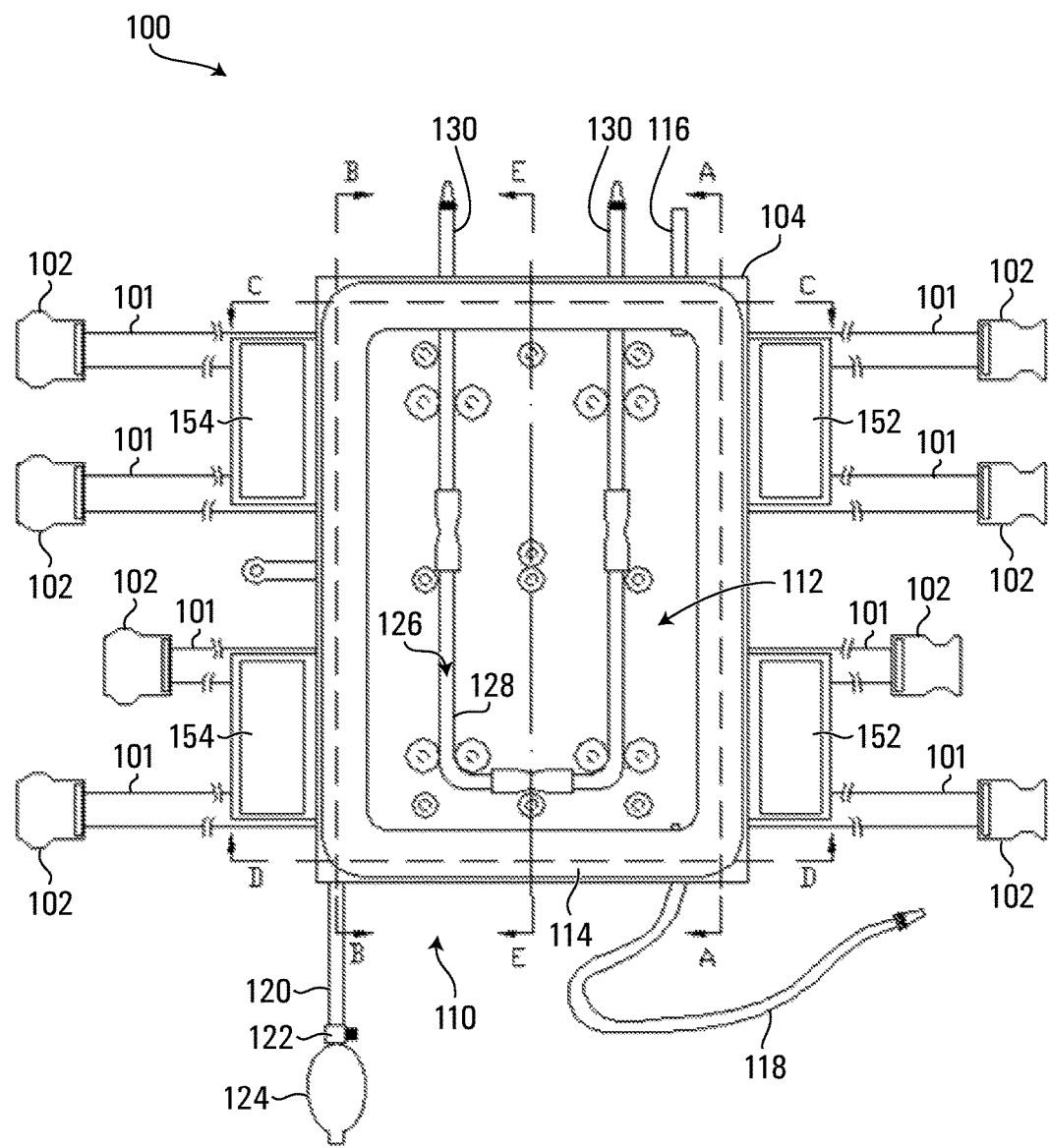
FIG. 2 is a schematic front view of the device of FIG. 1, with some detachable components removed from the base unit.

The inner channel 140 is in communication with a fluid source, such as pump 124 through a fluid valve, such as vale 122. A suitable pressurizing device may be used to push the fluid into the inner channel to inflate the seal. For example, a hand-held air pump or air blower with a bulb shape (as illustrated in FIG. 2 by pump 124) may be used as the pressurizing device. The ambient air may be used as the fluid source. The valve may be open for inflating or deflating the air and is closed to hold the pressure in the inner channel.

The inflatable seal material may be integrally formed with the wearable body, or may be glued to the base body. The brim of the tub (i.e., the top peripheral edge of the base body) may have a flat surface, or may have a groove for receiving the seal to reduce the height of the seal above the surface of the base body. In any event, when the seal is inflated, the seal material will expand and project out from the body surface to provide a sealing contact with the skin of the user.

The seal can prevent leakage of the soaking fluid. It is more comfortable for the user and can reduce the usage of the fluid when leakage of the soaking fluid is prevented.

Figure 2A:
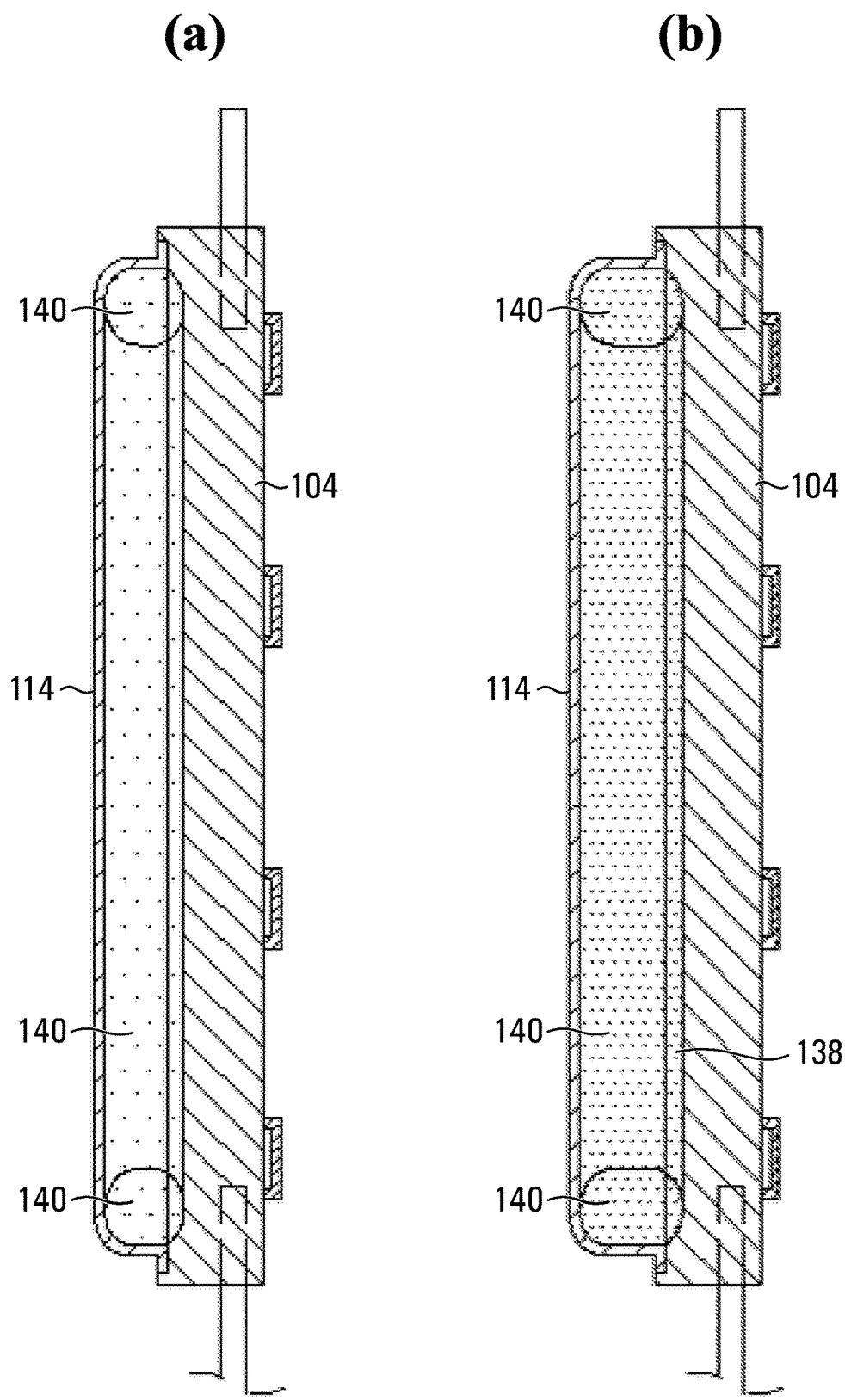
FIGS. 2A, 2B, 2C, 2D, and 2E are sectional views of the device of FIG. 2, taken along the lines A-A, B-B, C-C, D-D, and E-E respectively.
Figure 2B:
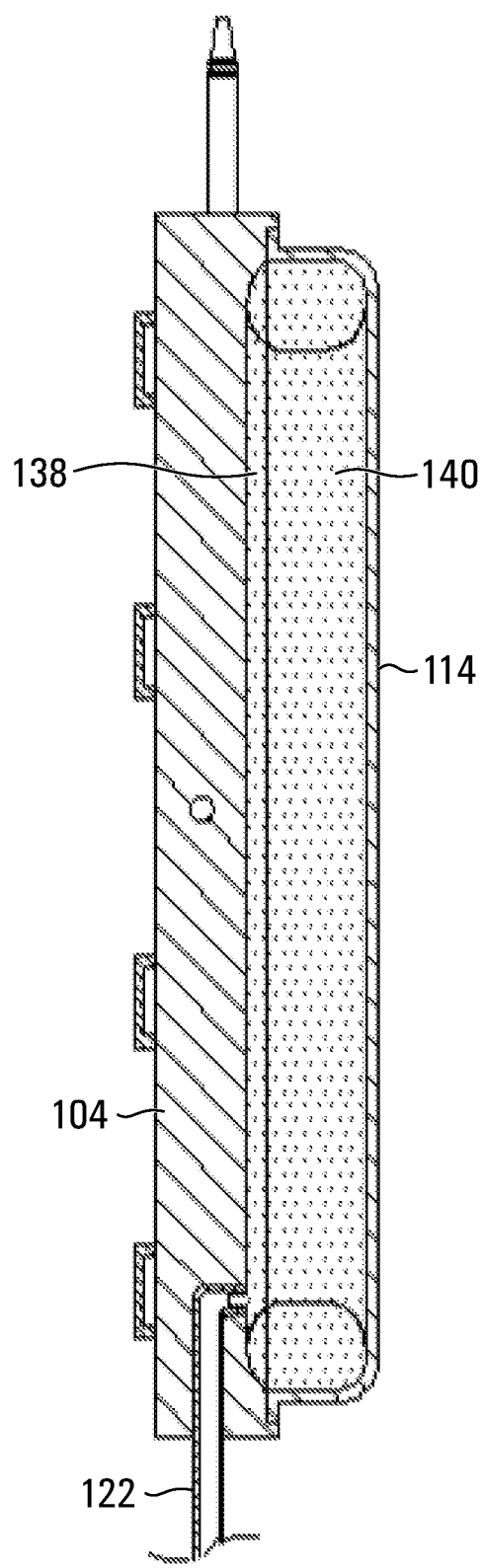
Figure 2C:
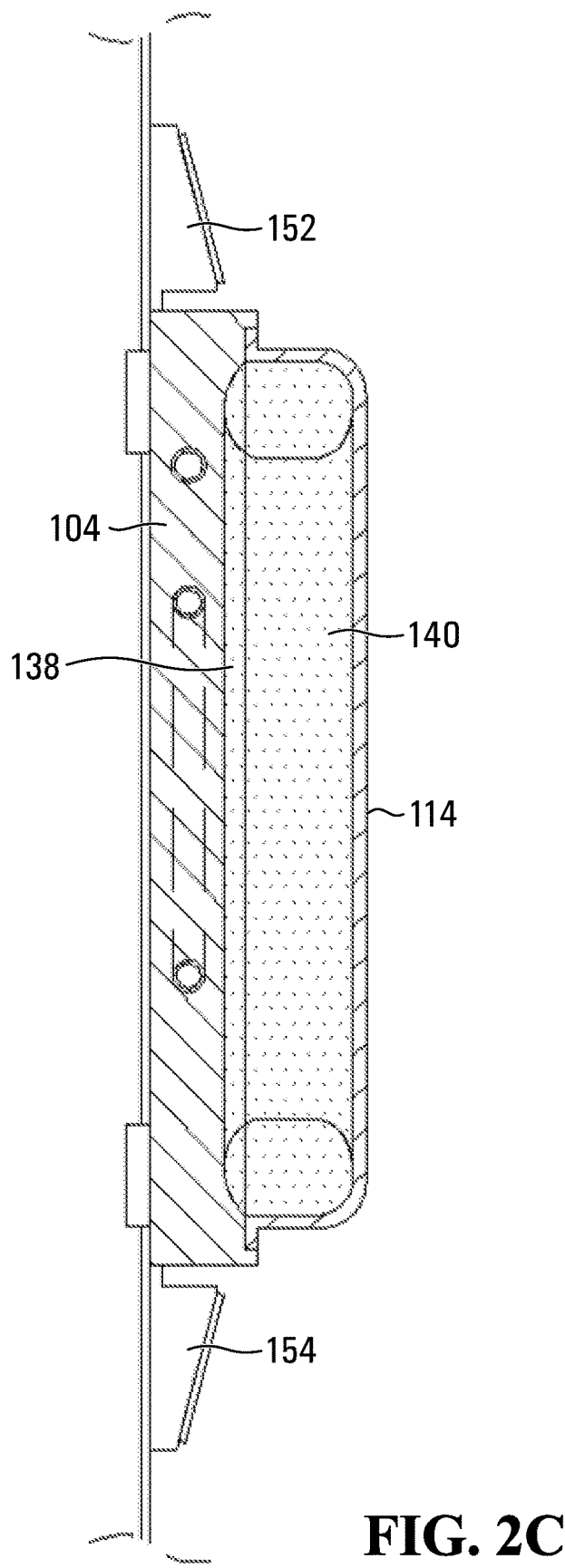
Figure 2D:
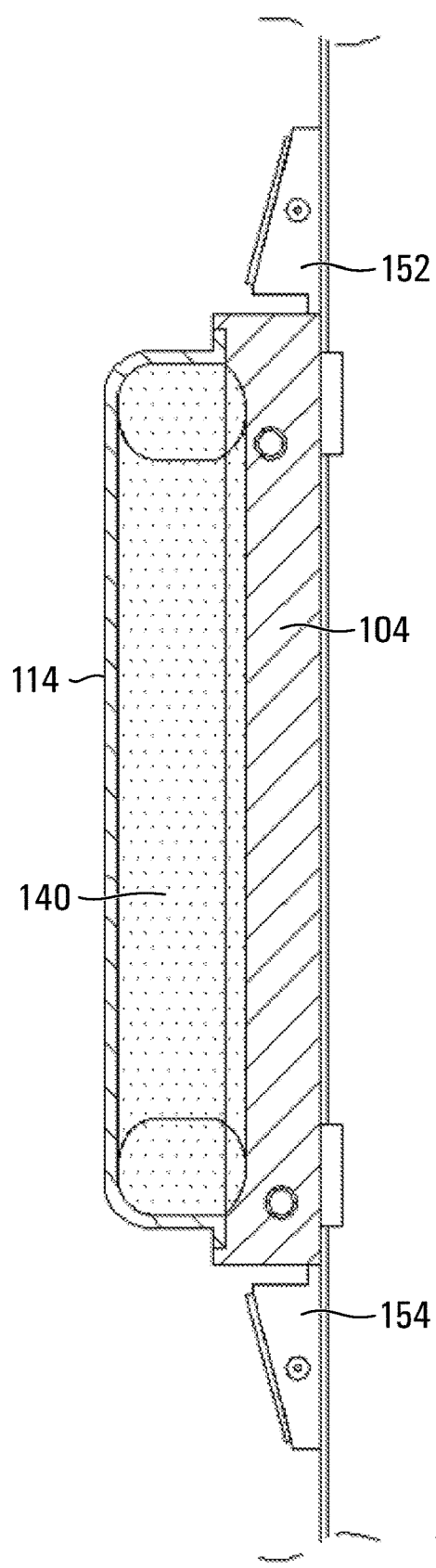
Figure 2E:
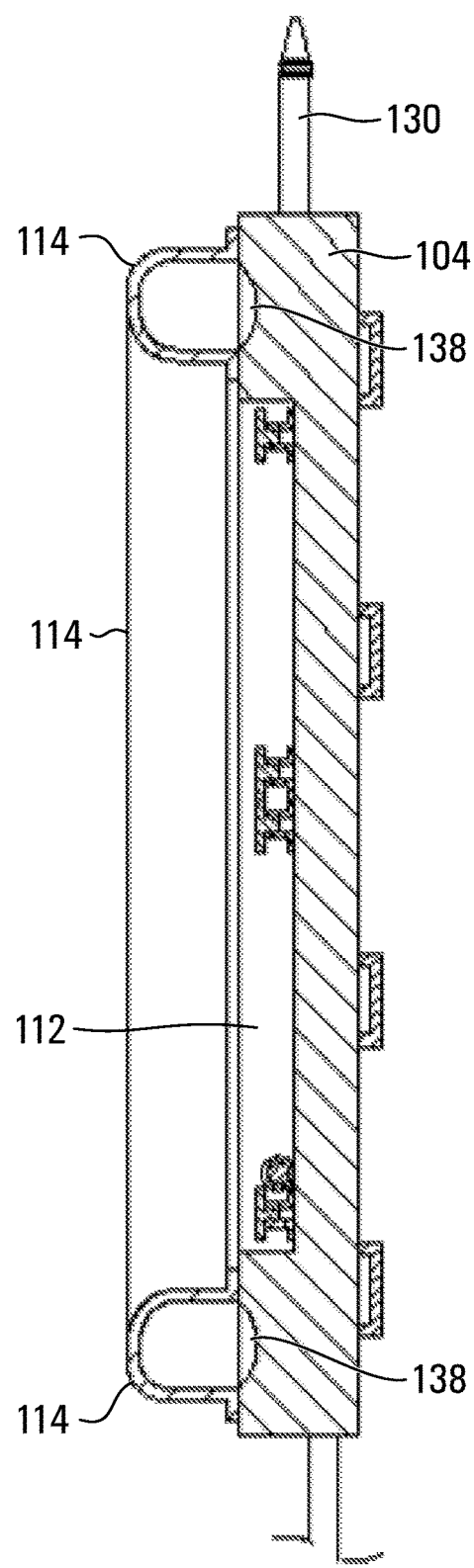

As depicted in FIGS. 2A-2E, base body 104 has a groove 138 formed along the periphery of tub 112, and seal 114, which is formed of a resilient silicone gel material, is glued to the based body 104 above the groove 138, so that the seal 114 and groove 138 define an inner channel 140. Initially, inner channel 140 is filled with atmospheric air at ambient pressure. During use, when sealing is required, pressured air is pumped into the inner channel 140 through conduit 120 (see e.g. FIG. 2B), which causes the seal 114 to expand and forming a tight seal around tub 112. As illustrated in FIG. 2A, when inner channel 140 is filled with pressured air, seal 114 tend to expand and thus applying a higher sealing pressure on the user skin. Even if no appreciable increase in volume of the seal is observed, the increased pressure in the seal can still provide a tighter seal between the skin and device 100.

The base body 104 may be formed of a soft material or rigid material, such as a silicone material with a suitable grade.

Suitable silicone materials for forming various components of device 100 may include $SiO_2$, dimethyl carbonate (DMC), and decytriglycol ($C_{16}H_{34}O_4$). For achieving desirable colors, a color filler may also be included.

The soaker 110 or its variation may have any suitable size or shape, which may be selected based on the body part of the user to be soaked and treated.

In some embodiments, an absorbent layer (not shown) may be provided in tub 112. The absorbent layer may be formed of cotton or another suitable material.

As discussed above, for convenient use, a temperature sensor and a temperature control mechanism may be provided. The temperature sensor may be connected to a display device to indicate the current temperature of the soaking liquid. The temperature control mechanism may include a heater and a cooling tubing. The heater may be an electrical heater. Alternatively, the heater may be a tubing that can be filled with hot water or another heated fluid. The cooling tubing may be filled with a coolant. The temperature may be controlled automatically or manually. In some embodiments, the heating may be controlled automatically with an electrical heater. A controller may be provided to control the heater based on the temperature signal received from the temperature sensor. Suitable conventional temperature sensors, controllers and heaters may be readily adapted for use in the device for this purpose.

As can be appreciated, for safety and for optimal treatment, the temperature of soaking fluid should be controlled and regulated to be within a predefined range. If the temperature is too high or too low, it would not be comfortable or even harmful to the user. For simplicity, cooling may be effected by simply passing room temperature or cold tap water through the cooling tubing. The inlet of the cooling tubing may be attached to a flexible pipe for receiving the tap water.

In the illustrated embodiment, tub 112 has an inlet 116 and an outlet 118 for introducing and releasing the soaking liquid, as can be better seen in FIG. 2.

Figure 3:
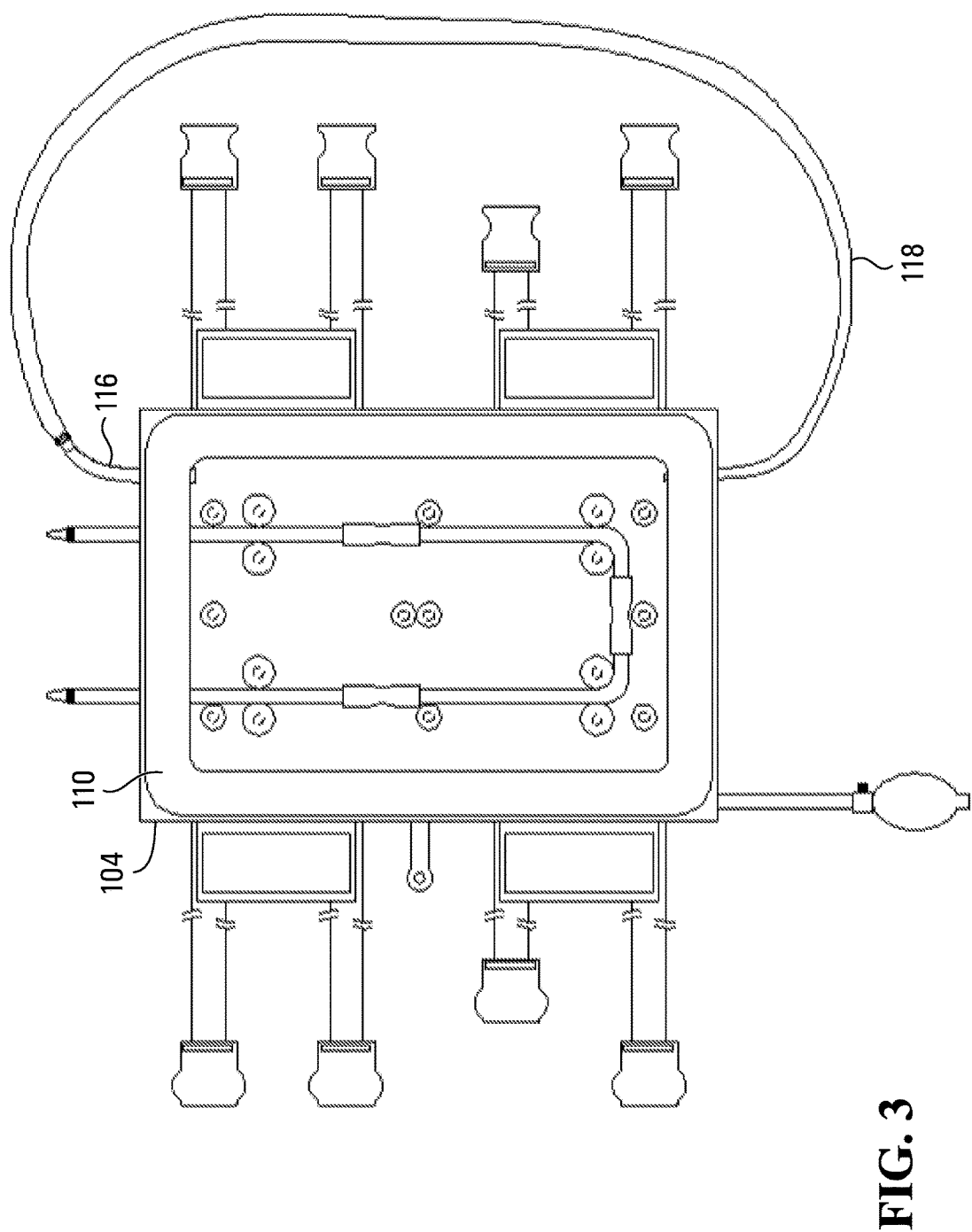
FIG. 3 is schematic front view of the device of FIG. 2 with a different configuration.
Figure 4:
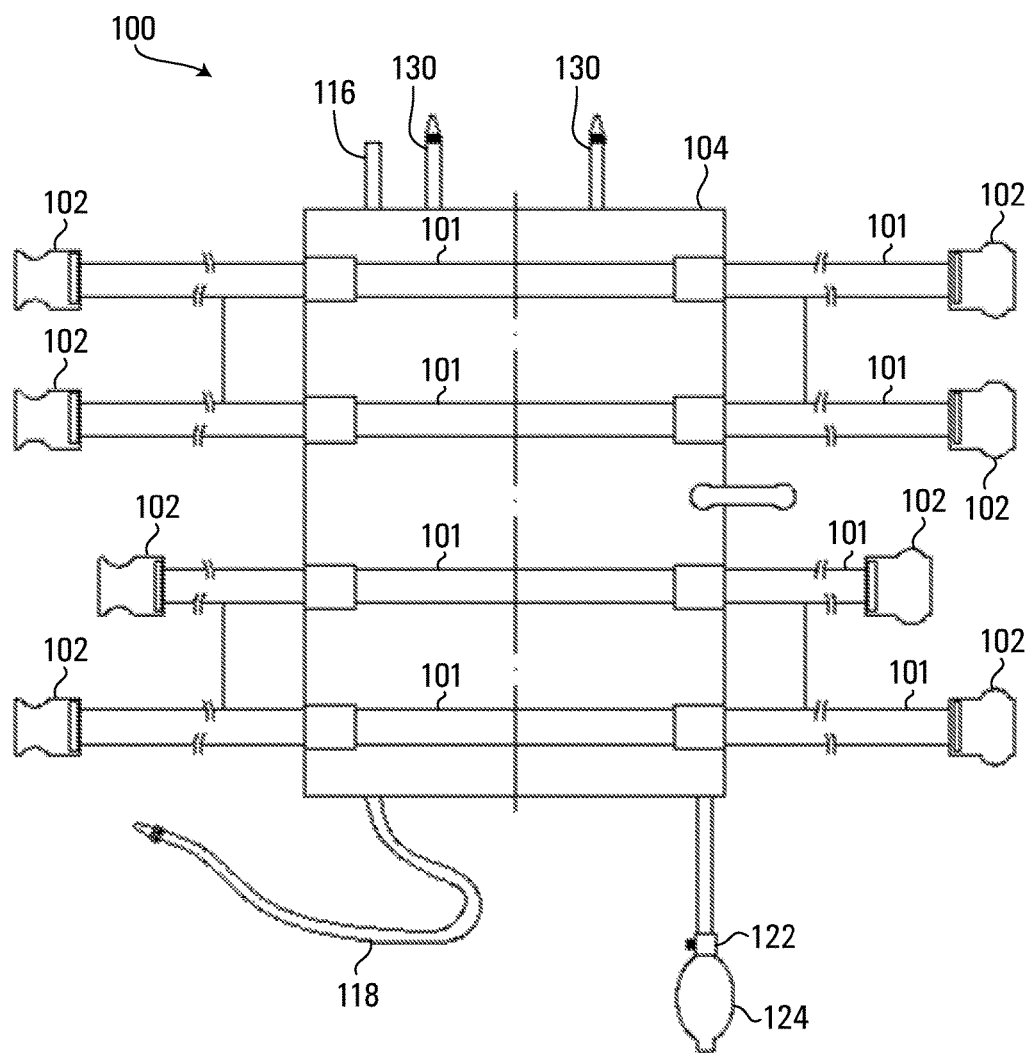
FIG. 4 is a schematic rear view of the device of FIG. 2.
Figure 5:
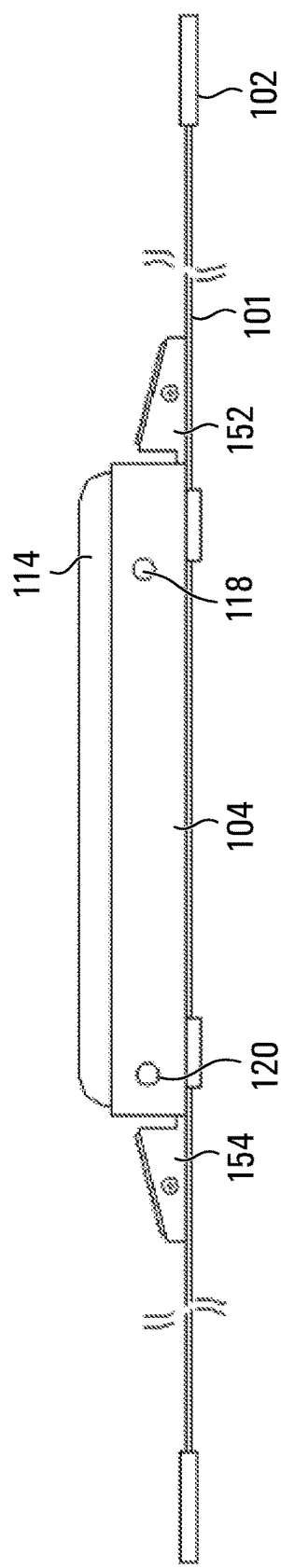
FIG. 5 is a schematic bottom view of the device of FIG. 2.
Figure 6:
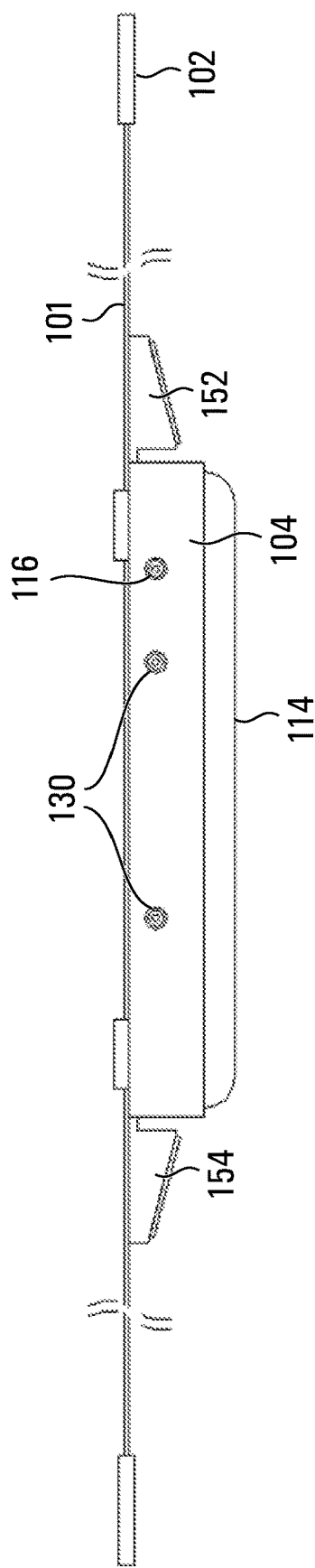
FIG. 6 is a schematic top view of the device of FIG. 2.
Figure 7:
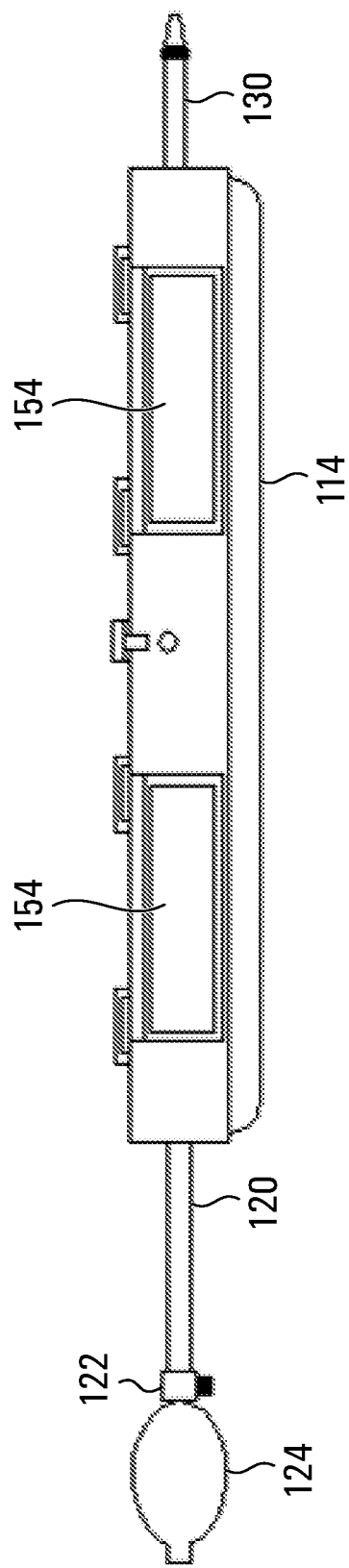
FIG. 7 is a schematic left elevation view of the device of FIG. 2.
Figure 8:
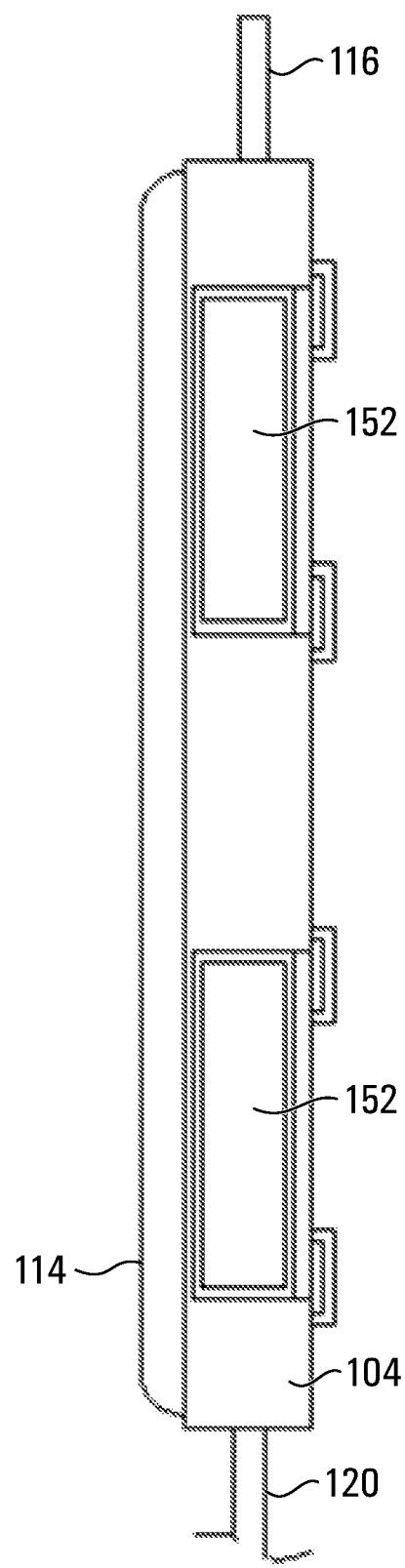
FIG. 8 is a schematic right elevation view of the device of FIG. 2.

The soaking liquid may be circulated through the tub 112 during use in some embodiments, where a liquid source (not shown) is attached and connected to the wearable device 100. In this case, the temperature control mechanism may be provided outside the wearable device 100. Alternatively, inlet 116 and 118 may be closed during use so that the soaking liquid is contained in tub 112 during a treatment session, as illustrated in FIG. 3.

The stimulator may be a massager, with massaging heads formed of the electrodes. Combined soaking and massaging treatment may provide improved treatment results.

Any conventional features and components of an electrical massager or stimulator may be provided. The massager may operate at any suitable stimulation frequencies conventionally used in massage treatments. In some embodiments, the stimulation frequency may be in the low to mid frequency ranges, such as from about 1 to 150 Hz, or 1 to 330 Hz.

The electrical stimulator may include power wires and signal wires, as will be understood by those skilled in the art. The wires may be connected to a controller and a power source respectively as in any conventional massaging device, and may pass through the wearable body. A massaging controller may be provided for the user to select the power, frequency and mode of operation. The massaging controller may be constructed according to any suitable massaging controller known to those skilled in the art.

The stimulator may be battery-powered, or powered by a powerline through an adaptor, or otherwise powered.

Figure 9:
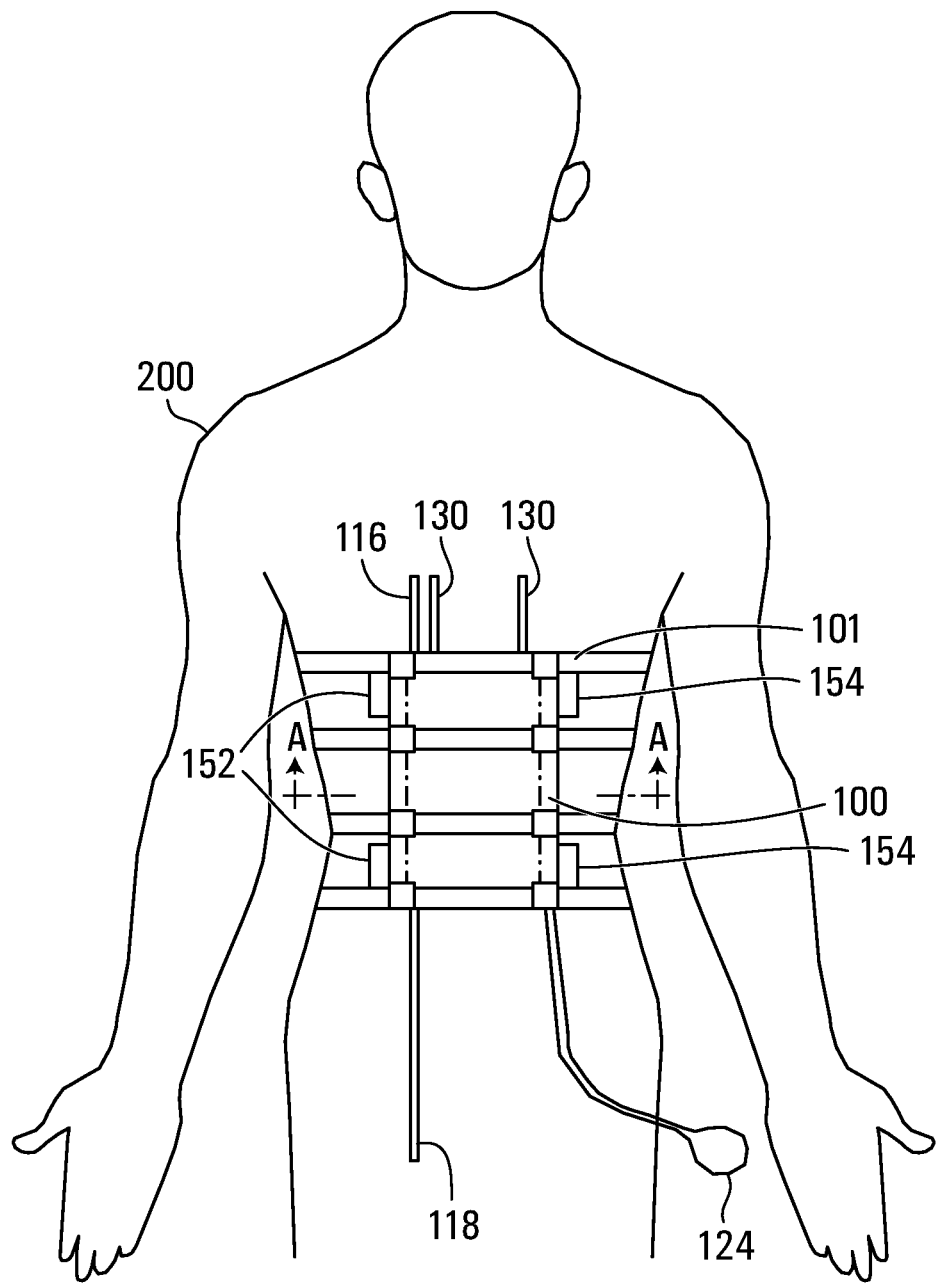
FIG. 9 is a schematic view of a user wearing the device of FIG. 2 at the back of the user.

During use, device 100 is worn by a user 200 as illustrated in FIG. 9, and the seal 114 (not visible in FIG. 9) is in direct contact with the skin of the user 200. Opposite ends of straps 101 are engaged using buckles 102 (not visible in FIG. 9) and the straps 101 are tightened so that while device 100 is worn comfortably by user 200, a sufficient pressure is applied to the user's skin at the contact regions beneath seal 114. Tub 112 (not visible in FIG. 9) and the skin on the back of the user 200 thus form a closed fluid chamber therebetween.

Figure 9A:
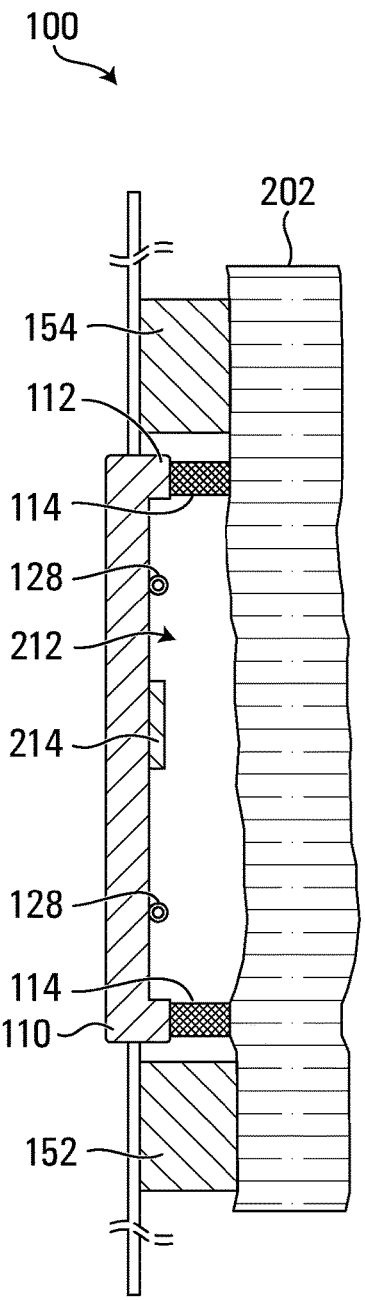
FIGS. 9A and 9B are schematic cross-sectional view of a fluid chamber formed between the device and the skin of the user of FIG. 9, along lines A-A in FIG. 9.
Figure 9B:
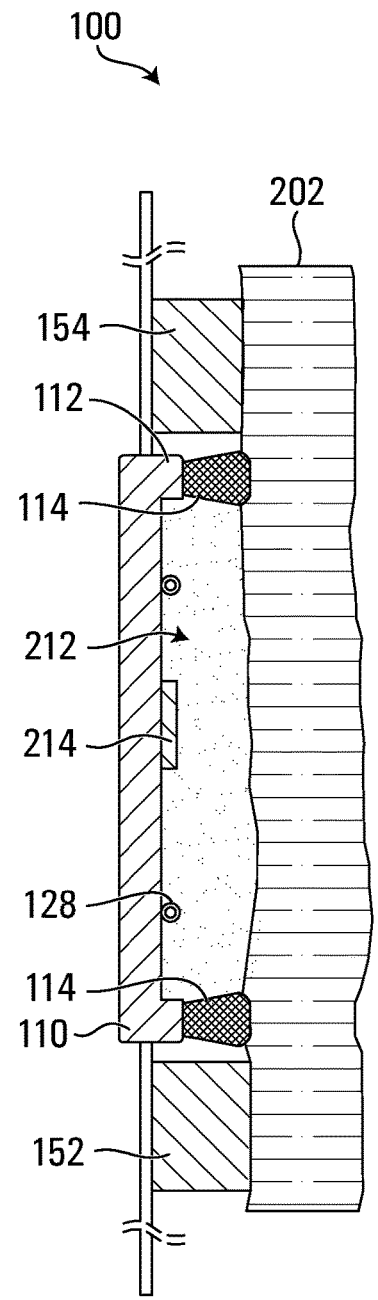

The operation of device 100 during use is also schematically illustrated in FIGS. 9A and 9B. As shown, the seal 114 and electrodes 152, 154 are in contact with the skin 202 of the user 200. FIG. 9A shows the state in which seal 114 is deflated and FIG. 9B shows the state in which seal 114 is inflated.

For ease of viewing and understanding, some components of device 100 are omitted in FIGS. 9A and 9B. For illustration purpose only, it is assumed that heat-exchange tubing 128 is used to cool the treatment fluid in this example, and a heating pad 214 is used to heat the treatment fluid if needed.

Seal 114 is inflated by pumping pressured air into inner channel 140 through conduit 120, with air pump 124. After a sufficient pressure has been reached and adequate sealing engagement between the skin 202 and device 100 can be obtained, valve 122 is closed to maintain the air pressure in seal 114 during treatment.

As can be seen in FIGS. 9A and 9B, the tub 112 and the skin 202 of the user 200 form an enclosed chamber 212 therebetween.

A heated treatment fluid (not shown) can be introduced into chamber 212 through fluid inlet tubing 116 after straps 101 of device 100 are tightened and seal 114 is inflated so that a fluid tight seal is formed between seal 114 and the skin 202.

With the fluid tight sealing engagement intact, a soaking liquid is introduced into the fluid chamber 212 formed by the tub 112 and the user skin 202 for treatment, through inlet tubing 116. Outlet tubing 118 may be closed, or its terminal end may be elevated to above base body 104, to prevent premature discharge of the treatment from the fluid chamber. For example, after loading of the soaking (treatment) liquid, the terminal ends of inlet tubing 116 and outlet tubing 118 may be sealingly connected to prevent leakage of the treatment liquid from tubing 116 and 118.

The treatment liquid may be any suitable liquid for physiotherapeutic treatment. For example, the liquid may include water, an aqueous based solution, an alcohol, or an alcohol based solution. Desired or selected herbal components may be included in the treatment liquid. The treatment liquid may be pre-heated, or pre-cooled depending on the desired effects.

The volume in the fluid chamber 212 is sufficient to provide a pool of the soaking liquid in the fluid chamber 212.

During treatment, the temperature of the treatment liquid may be controlled or regulated, such as by selectively heating or cooling using heat-exchanger 126 and heating pad 214.

As can be appreciated by those skilled in the art, heating the treatment liquid may have one or more beneficial effects. For example, heat may assist in absorption of treatment materials into the user's body and relaxation of tight muscles, and may enhance the effect of massaging.

For cooling during or at the end of a treatment session, a coolant may be circulated through heat-exchange tubing 128 to cool the soaking liquid. The coolant may be tap water, ice water or chilled water, or the like. As an example, the coolant may be circulated using a water pump, such as YOSOO™ SC-300T 12 V DC low noise water pump with pump tank provided by Lianyungang Yosoo Industrial Technique Co., Ltd.

When the volume of the fluid in the fluid chamber 212 is sufficiently large to allow fluid flow, efficient heat distribution and quick temperature equilibrium can be achieved.

While the skin 202 is soaked with the treatment liquid, an electrical signal may be applied to each pair of electrodes 152, 154 to stimulate tissues under the skin soaked by the treatment liquid. The electrical signal may be applied using controller 158 through conductor lines 156 connected to the respective electrodes. Suitable stimulation frequency, amplitude and signal profile may be selected by the user 200 or another person using controller 158.

Conveniently, as a large volume (pool) of the treatment liquid is inside the tub 112, contraction or twitching of the user's muscle caused by electrical stimulation or massaging will shake or stir the treatment liquid and can cause bulk movement of the treatment liquid. Bulk movement of the treatment liquid can in turn produce a gentle impact on the skin, which may be beneficial.

Treatment temperature can be monitored and controlled either automatically or manually. The temperature may be regulated for treatment purpose, to prevent the temperature to become too high or too low so as to protect the user from being harmed or injured, and to keep the user comfortable. In this regard, a larger volume of the pool of the soaking fluid may be beneficial as it will help to avoid a sudden or quick change in temperature, or to prevent a local temperature from rising too quickly due to unexpected events such as malfunction of a heater or the like. As noted above, a larger volume of the fluid in the fluid chamber 212 has a larger heat capacity and can allow the temperature of the liquid to be more stably controlled.

A timer may be provided for control treatment time of both the electrical stimulation and the time the skin is exposed to the treatment fluid and to heating.

A combined soaking, heating and massaging treatment may provide a synergistic treatment effect.

During treatment, the user may walk around and is not confined to a fixed position. The user may also perform certain physical activities. Leakage of the treatment is prevented even when the user is performing these physical activities. As the device 100 is portable, the treatment can be conveniently carried out at any desired location, such as at the user's home or work place, in a hotel room, or during travel.

As alluded to earlier, a similar soaking physiotherapeutic device may also be sized and shaped to be worn over a shoulder, an arm, a leg, the chest or the belly of the user.

Figure 10:
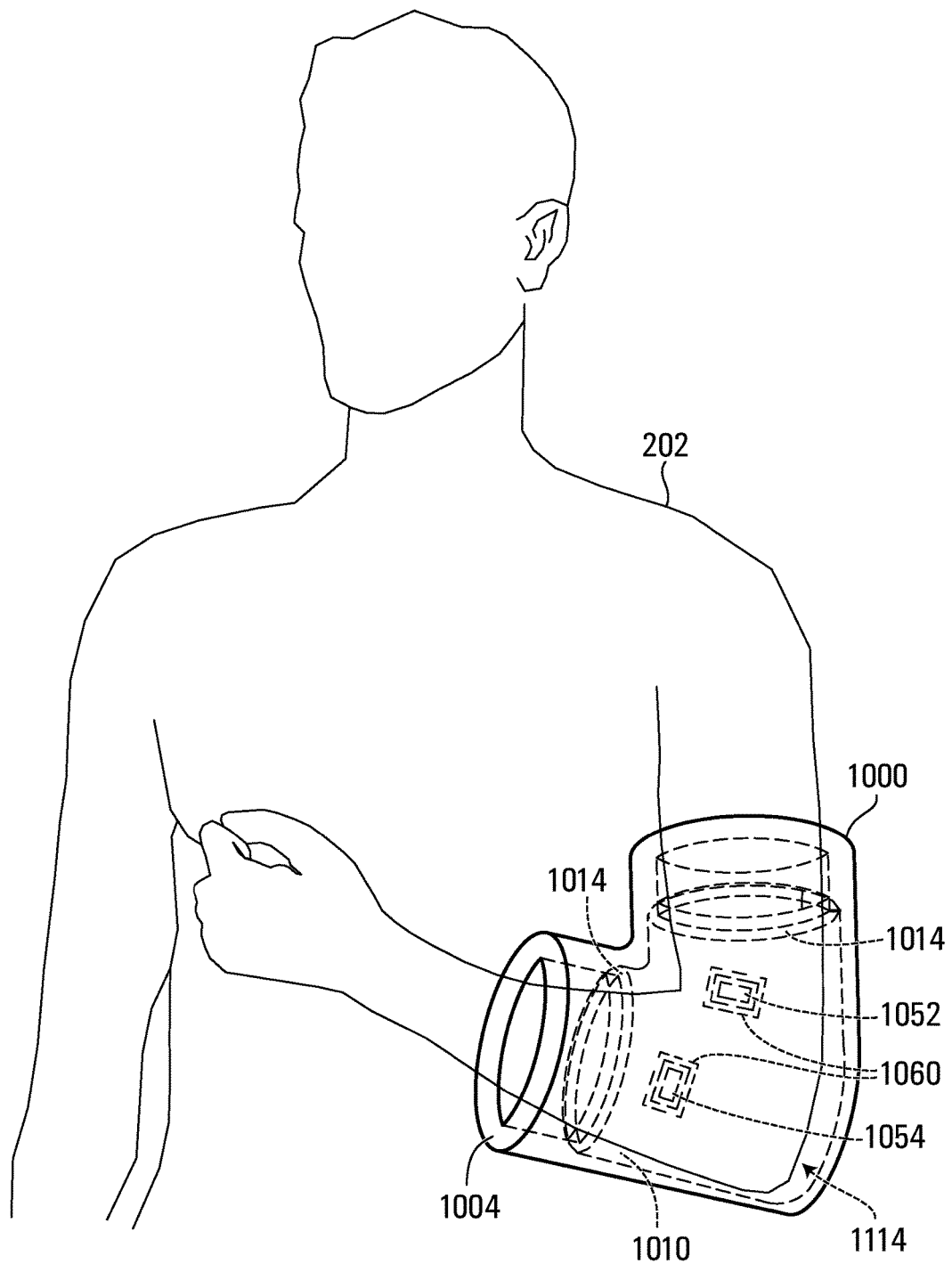
FIG. 10 is a schematic view of a user wearing a soaking physiotherapeutic device over an elbow of the user.

FIG. 10 illustrates a user 200 wearing a soaking physiotherapeutic device 1000 over an arm or elbow of the user 200. Device 1000 has base body 1004 formed of a flexible material so that body 1004 may be bent or straightened as the user 200 moves his forearm.

Device 1000 also includes a soaker 1010 and an electrical stimulator. However, for easy attachment and to prevent liquid leakage, the base body 1004 of device 1000 is tubular, and a pair of electrodes 1052 and 1054 for electric stimulation are disposed between two inflatable seals 1014 positioned near the end openings of the tubular base body 1004. An inflatable sealing ring 1060 is positioned near and around each electrode 1052 or 1054 for isolating the electrode 1052 or 1054 from the treatment liquid. A fluid chamber 1014 is formed between the soaker 1010 and the user's skin.

Figure 10A:
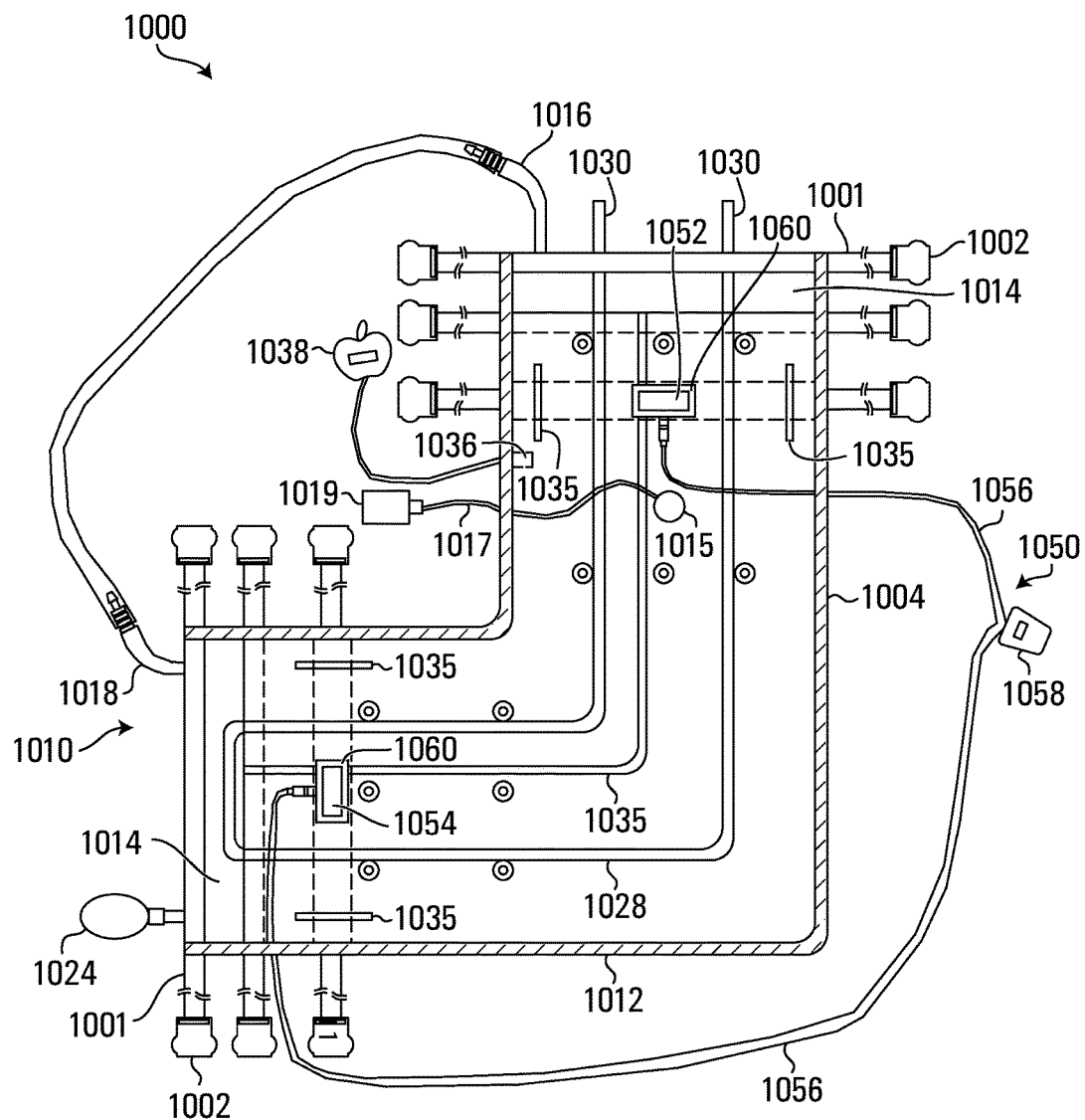
FIG. 10A is a schematic cross-sectional view of an embodiment of the soaking physiotherapeutic device of FIG. 10.

An embodiment of device 1000 may be constructed as illustrated in more detail in FIG. 10A. Specifically, device 1000 includes a soaker 1010 and an electrical stimulator 1050.

Soaker 1010 is similarly configured as soaker 110, and has a liquid tub 1012 formed by a cylindrical or tubular base or support body 1004. A resilient ring-shaped seal 1014 is provided at each one of the two ends of the tub 1012 for sealing engagement with the user's skin. A fluid inlet tubing 1016 and fluid outlet tubing 1018 are mounted on soaker 1010 for introducing the liquid into the fluid chamber and drain the liquid out of the fluid chamber respectively during use.

The electrodes 1052 and 1054 of the electrical stimulator 1050 are positioned within the tub 1012 and are each surrounded by a ring-shaped inflatable seal 1060. The electrodes 1052, 1054 are connected by wires 1056 to a controller and signal source 1058.

Seals 1014 and 1060 may be similarly constructed and operated as described above with regard to seal 1014. An air pump 1024 may be used to inflate the seals 1014 and 1060.

A heat-exchange tubing 1028 with inlet/outlet tubing 1030 is provided to control the temperature in the fluid chamber 1014. A heating pad 1015 is also mounted on the base body 1004 within tub 1112. The heating pad 1015 is connected by electrical wire 1017 to a power source and temperature controller 1019. A temperature sensor 1036 is mounted in the tub 1012, and connected to a temperature display device 1038.

Elastic straps 1001 are provided to tighten the ends of base body 1004 so that device 1000 can be secured to the arm of the user 200 and a fluid tight seal is provided between the seal 1014 and the user's skin on the arm.

To ensure sufficient sealing, a tightening strap 1001 may be placed directly over the portion of the base body 1004 that is behind each one of the electrodes 1052 and 1054, so that a tight seal can be formed at each sealing ring 1060. In some embodiments, a strap 1001 may include an air inflable channel in the strap so an additional pressure may be applied during use by inflating the strap after the strap has been tightened.

Ridges 1035 or similar protrusions from the base body 1004 towards the inner side of tub 1012 are provided to ensure sufficient room or space is provided within the fluid chamber to contain a sufficient volume of the soaking or treatment fluid. Without the ridges, the base body 1004 may collapse or bend inward under the pressure applied by the straps 1001 so as to leave little room in the fluid chamber, or block fluid circulation or communication with the fluid chamber such that heat distribution and temperature control may not be uniform within the fluid chamber.

Device 1000 may be similarly operated as device 100.

Figure 11:
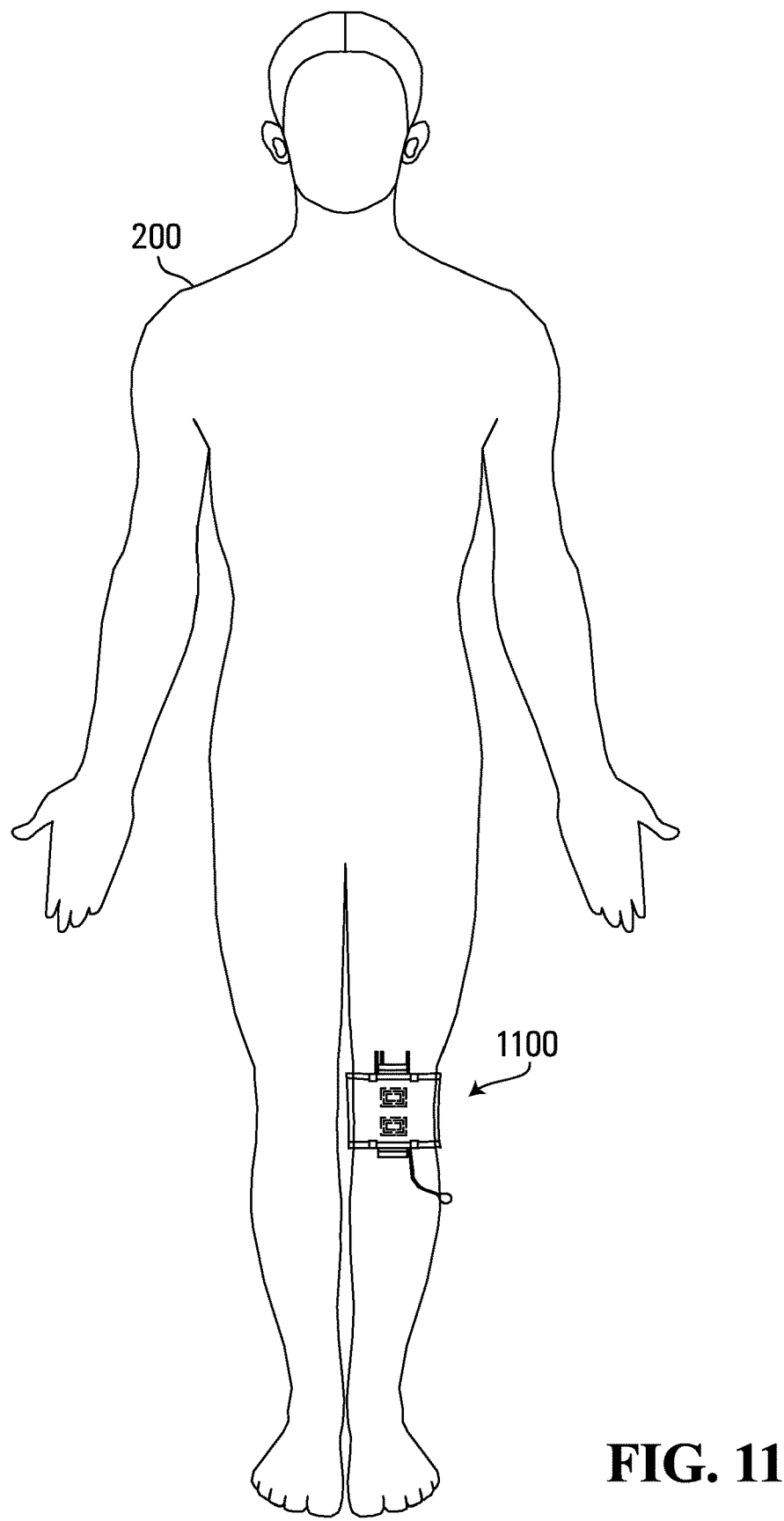
FIG. 11 is a schematic view of a user wearing a soaking physiotherapeutic device over a knee of the user.

FIG. 11 illustrates a user 200 wearing a soaking physiotherapeutic device 1100 over a leg or knee of the user 200. Device 1100 may configured similar to device 1000, but with a different size that fits the leg or knee of the user instead of the arm or elbow of the user.

Figure 11A:
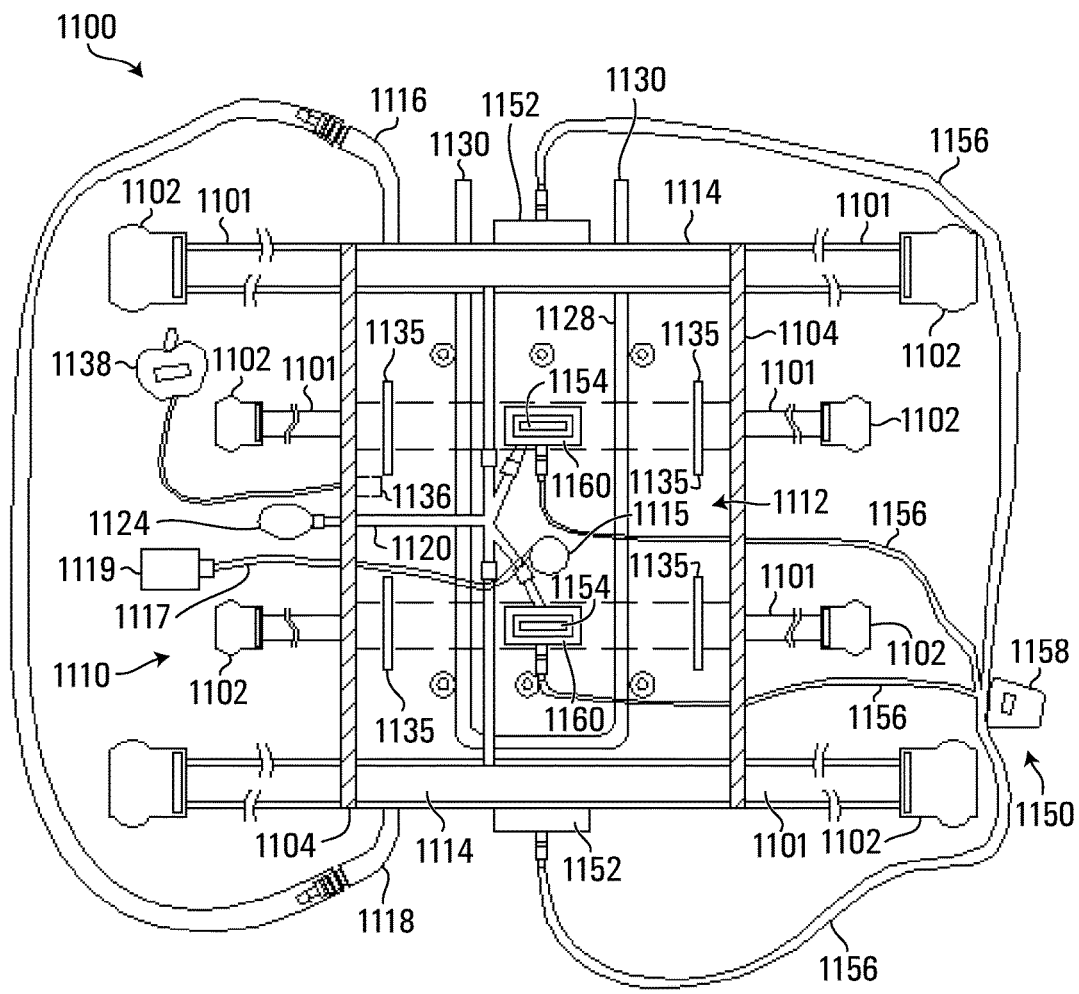
FIG. 11A is a schematic cross-sectional view of an embodiment of the soaking physiotherapeutic device of FIG. 11.

For illustration purposes, device 1100 is shown in FIG. 11A as having two pairs of electrodes 1152, 1154. A first pair is at the top as shown in FIG. 11A, and a second pair is shown at the bottom. For each pair of electrodes, one electrode 1152 is outside the tub 1112 and one electrode 1154 is inside the tube 1112. The electrodes 1152, 1154 are all insulated from the soaking liquid by either seals 1114 or seals 1160.

Otherwise, device 1110 is similar to device 1000 and like parts or components in device 1100 and device 1000 are numbered with the same trailing numbers. In particular, device 1100 has a soaker 1110, which include a liquid tub 1112 formed by a cylindrical or tubular base body 1104. Seals 1114 and 1160 are provided for sealing the fluid chamber and isolating the electrodes 1152, 1154. Fluid inlet tubing 1116 and fluid outlet tubing 1118 are mounted on soaker 1110 for introducing the liquid into the fluid chamber and drain the liquid out of the fluid chamber respectively during use.

The electrodes 1152, 1154 are connected by wires 1156 to a controller and signal source 1158.

An air pump 1124 may be used to inflate the seals 1014 and 1060.

A heat-exchange tubing 1128 with inlet/outlet tubing 1130 is provided in the tub 1112. Also provided are a heating pad 1115 connected by electrical wire 1117 to a temperature controller 1119, and a temperature sensor 1136 connected to a temperature display device 1138. Ridges 1135 similar to ridges 1035 are also provided in tub 1112.

Straps 1101 and buckles 1102 are provided at the back of the base body 1104 for attaching the device 1100 to the user 200, and apply pressure to seal the fluid chamber.

In some embodiments, a strap 1101 may include an air inflable channel in the strap so an additional pressure may be applied during use by inflating the strap after the strap has been tightened.

Device 1100 may be similarly operated as device 1000.

Figure 11B:
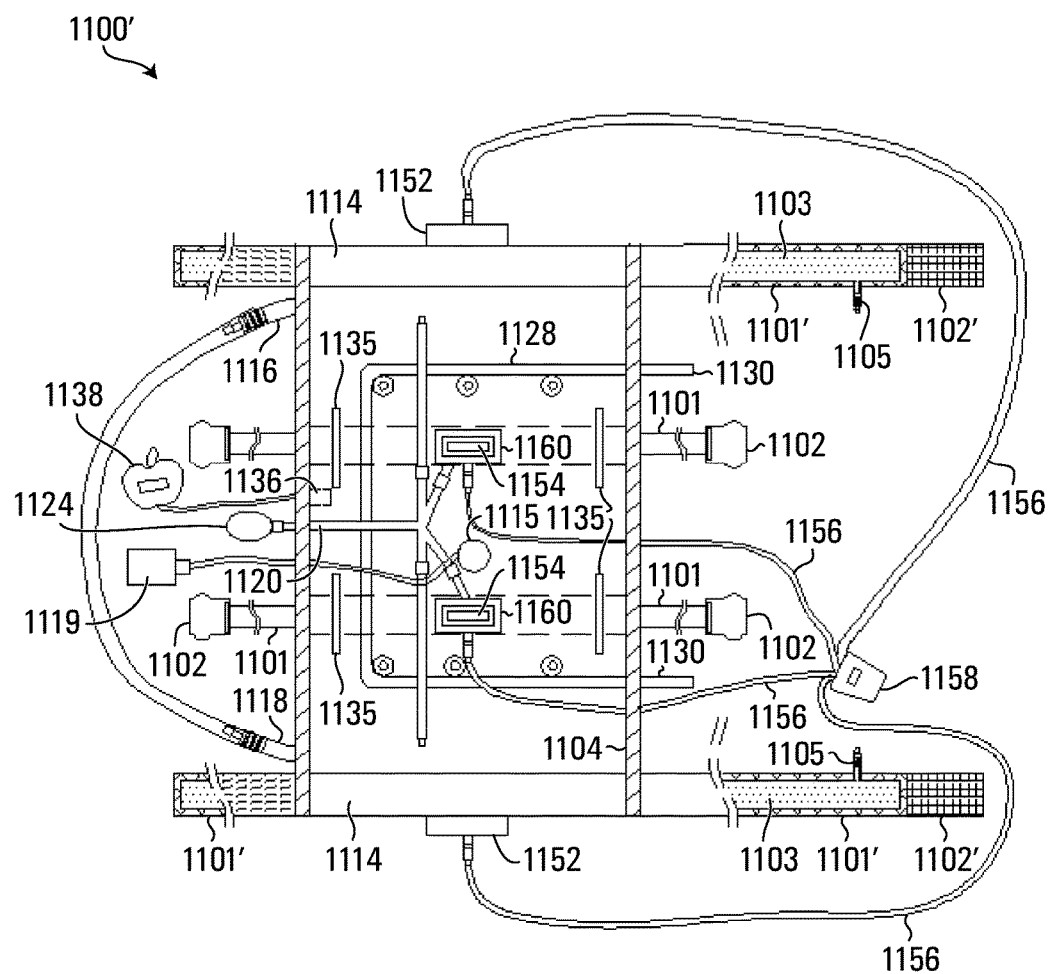
FIG. 11B is a schematic cross-sectional view of a variant of the device of FIG. 11A.

A variant of Device 1100, device 1100' is illustrated in FIG. 11B. As depicted, device 1100' is similar to device 1100 except the differences discussed next. Like components are denoted with like reference numerals in FIGS. 11A and 11B, and are not reiterated. However, it is noted that the orientation and configuration of some components may be different as illustrated. For example, heat-exchange tubing 1128, and inlet/outlets 1116, 1118, and 1130 may be configured as shown in FIG. 11B. Further, straps 1101' are different from straps 1101. Each Strap 1101' has an inflatable channel section 1103, which may be inflated by pumping air into the channel through an air inlet 1105. The ends of strap 1101' are provided with hook and loop or hook-and-pile fastener pads 1102', which can be quickly attached to one another. During use, the straps 1101' may be inflated after the straps 1101' have been tightened and the end pads 1202' have been attached and secured in place. FIGS. 11E and 11F show cross-section views of the strap 1101' in a deflated state (FIG. 11E) and an inflated state (FIG. 11F). Inflation of straps 1101' can apply additional pressure to ensure the engagement between the skin and the device 1100' is sealed.

Figure 11C:
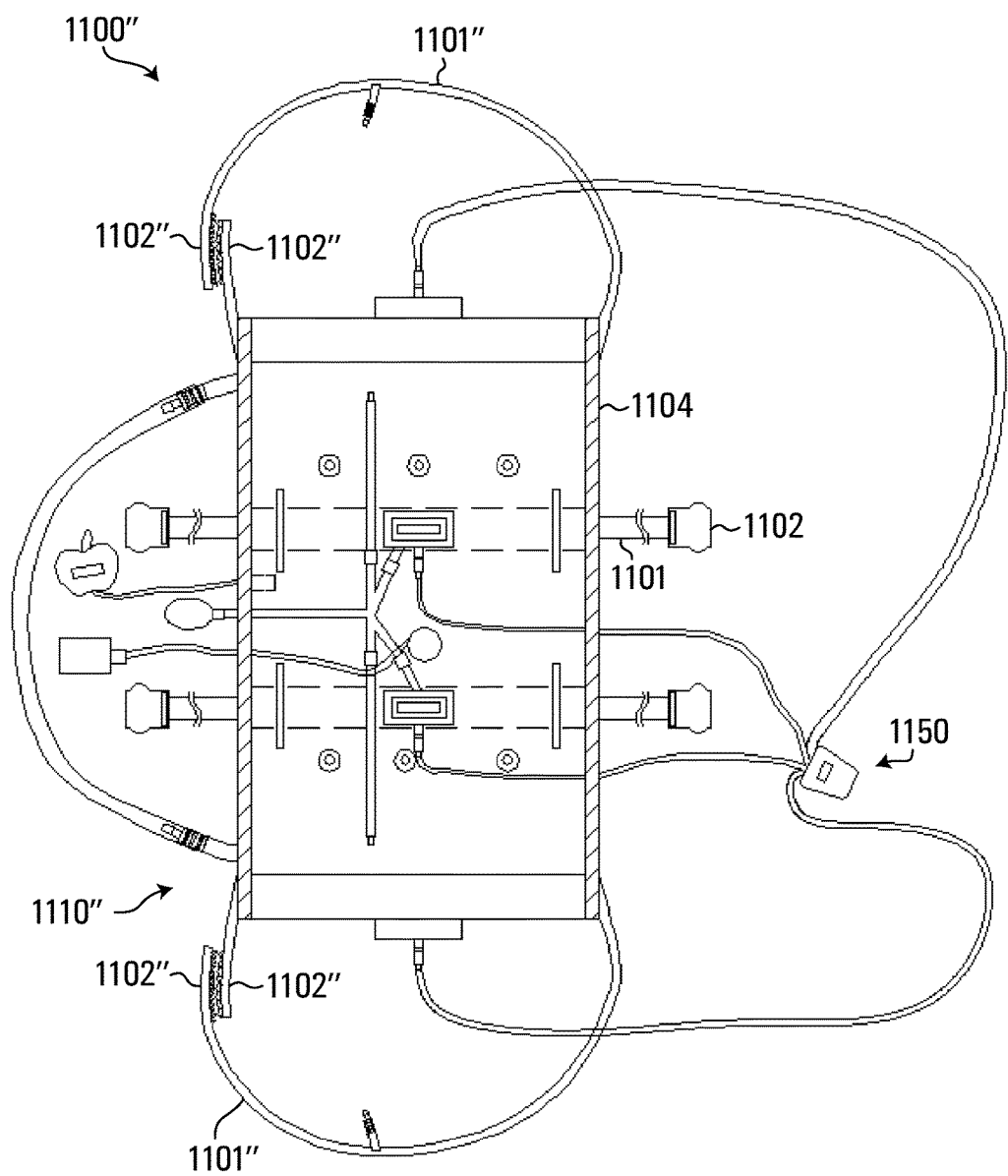
FIGS. 11C and 11D are schematic cross-sectional views of another variant of the device of FIG. 11A, in two different states.
Figure 11D:
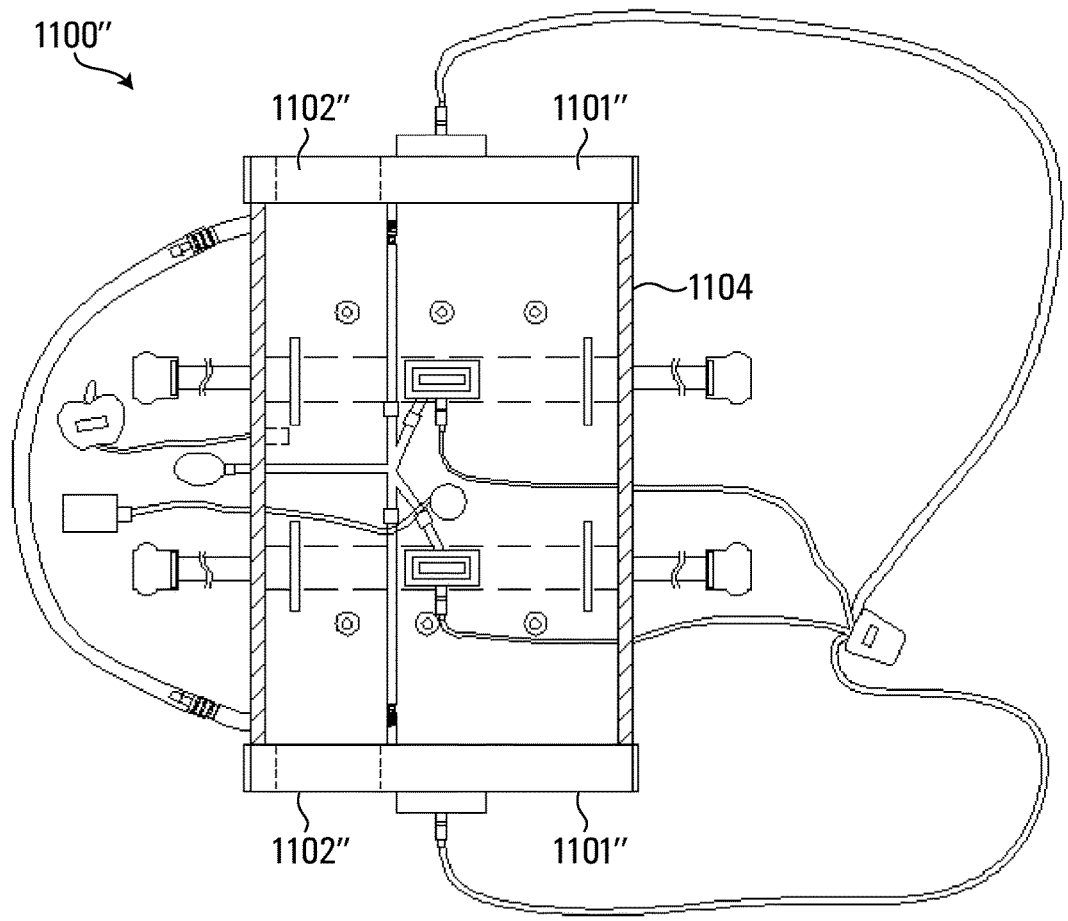
Figure 11F:
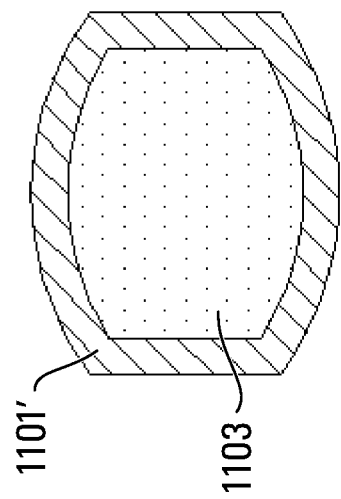
FIGS. 11E and 11F are cross-sectional views of the strap of device of FIG. 11B, in deflated and inflated states respectively.
Figure 11E:
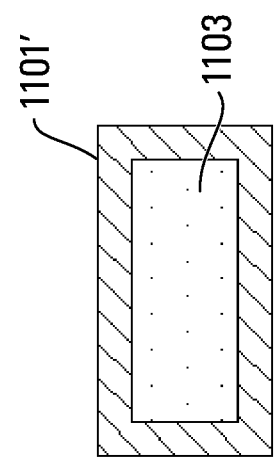

FIG. 11C illustrates another variant, Device 1100". Device 1100" is similar to device 1100' except that the soaker unit 1110" in device 1100" does not include a heat-exchange tubing, and straps 1101" are configured and oriented differently. FIG. 11D shows device 1100" in a state where the straps 1101" are tightened and attached to one another, and the fastener pads 1102" are attached.

Figure 12:
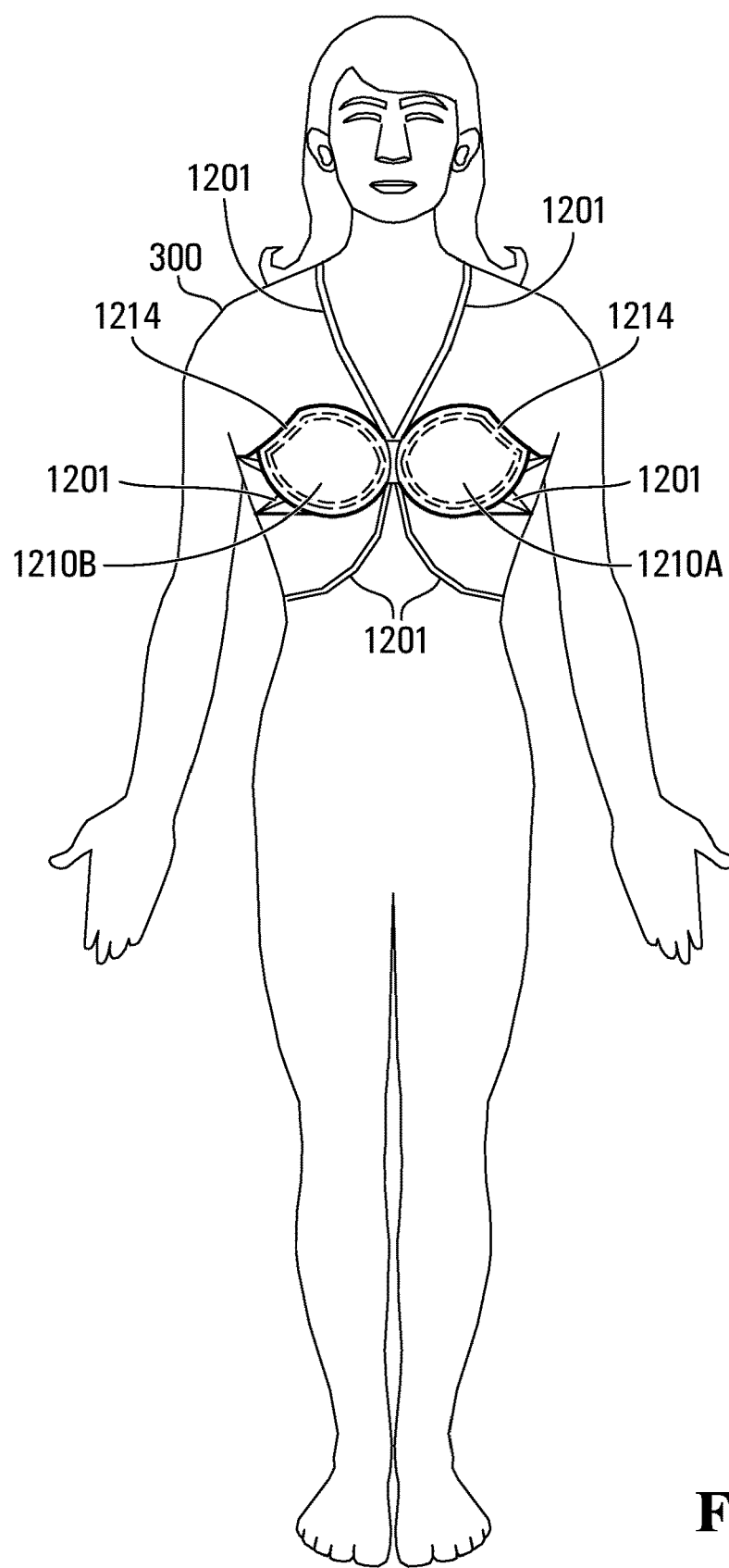
FIG. 12 is a schematic view of a user wearing a soaking physiotherapeutic device over the chest of the user.

FIG. 12 illustrates a user 300 wearing a soaking physiotherapeutic device 1200 over her chest.

Figure 12A:
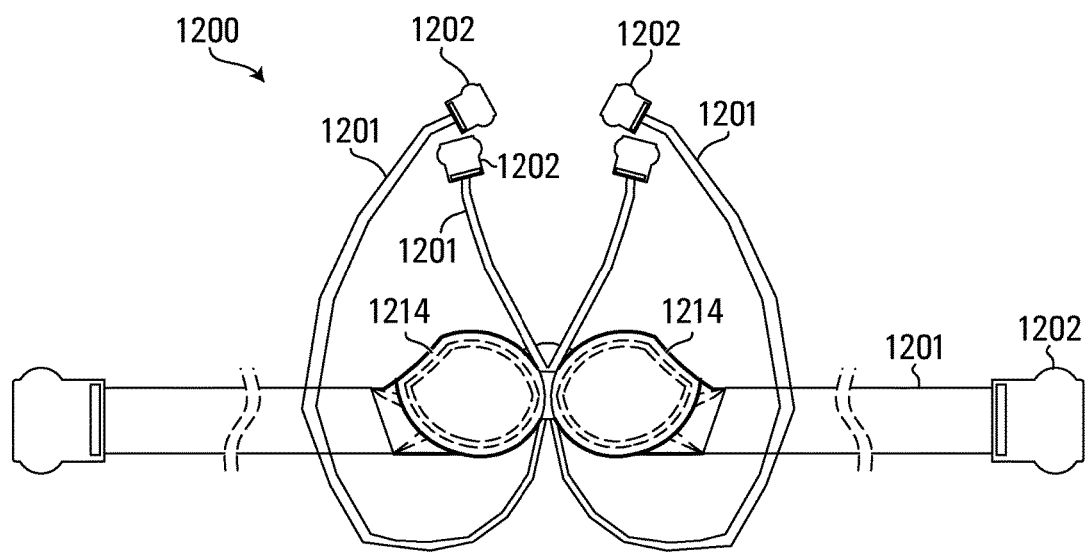
FIG. 12A is a schematic front view of an embodiment of the soaking physiotherapeutic device of FIG. 12.
Figure 12B:
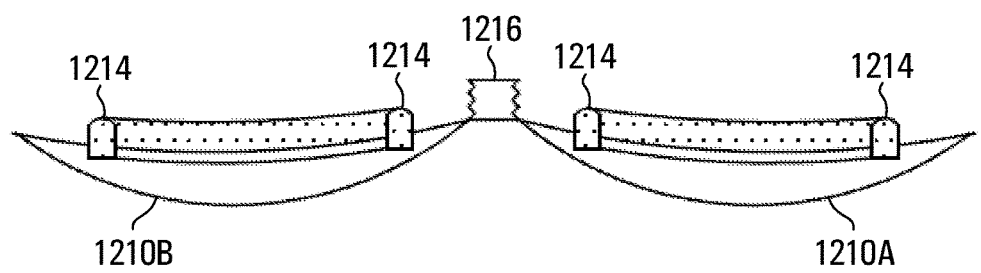
FIG. 12B is a partial top view of the device of FIG. 12A with the seal deflated.
Figure 12C:
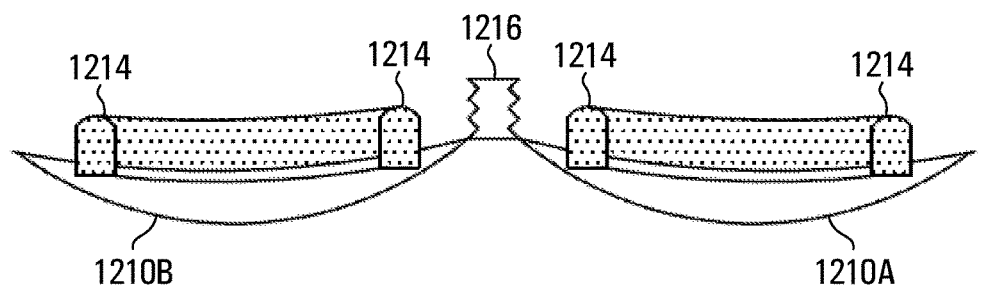
FIG. 12C is a top view of the partial device of FIG. 12B with the seal inflated.

FIGS. 12A, 12B and 12C further illustrates device 1200, which may also have an electrical stimulator (but not shown for simplicity and easier viewing). Device 1200 has two soaking units 1210A and 1210B (also collectively or individually referred to as soaking unit 1210) and straps 1201 for attaching device 1200 to the user's chest. Device 1200 may be shaped and sized like a bra. An inflatable seal 1214 is provided at the periphery of each soaking unit 1210 for preventing leakage of the treatment fluid. Each soaking unit 1210 and the electrical stimulator may be similarly constructed as the soaker and electrical stimulator in device 100, 1000 or 1100, but with modifications to suit the special requirements to fit over the user's chest.

The seals 1214 may be deflated as shown in FIG. 12B, or inflated as shown in FIG. 12C to seal the fluid chamber formed between device 1200 and the user's skin.

For conveniently attaching and securing device 1200 to the user 300, device 1200 may include a height adjustment mechanism 1216 in the middle (bridge) portion between soaking units 1210A and 1210B. After device 1200 is affixed to the user's body with cross straps 1201, the height adjustment mechanism 1216 may be adjusted to rise against the tension applied by the straps 1201. The height of the middle portion of device 1200 may be adjusted with a pneumatic device, mechanical device or a motor-actuated device (not expressly shown).

Device 1200 may be similarly operated as device 100.

Figure 13:
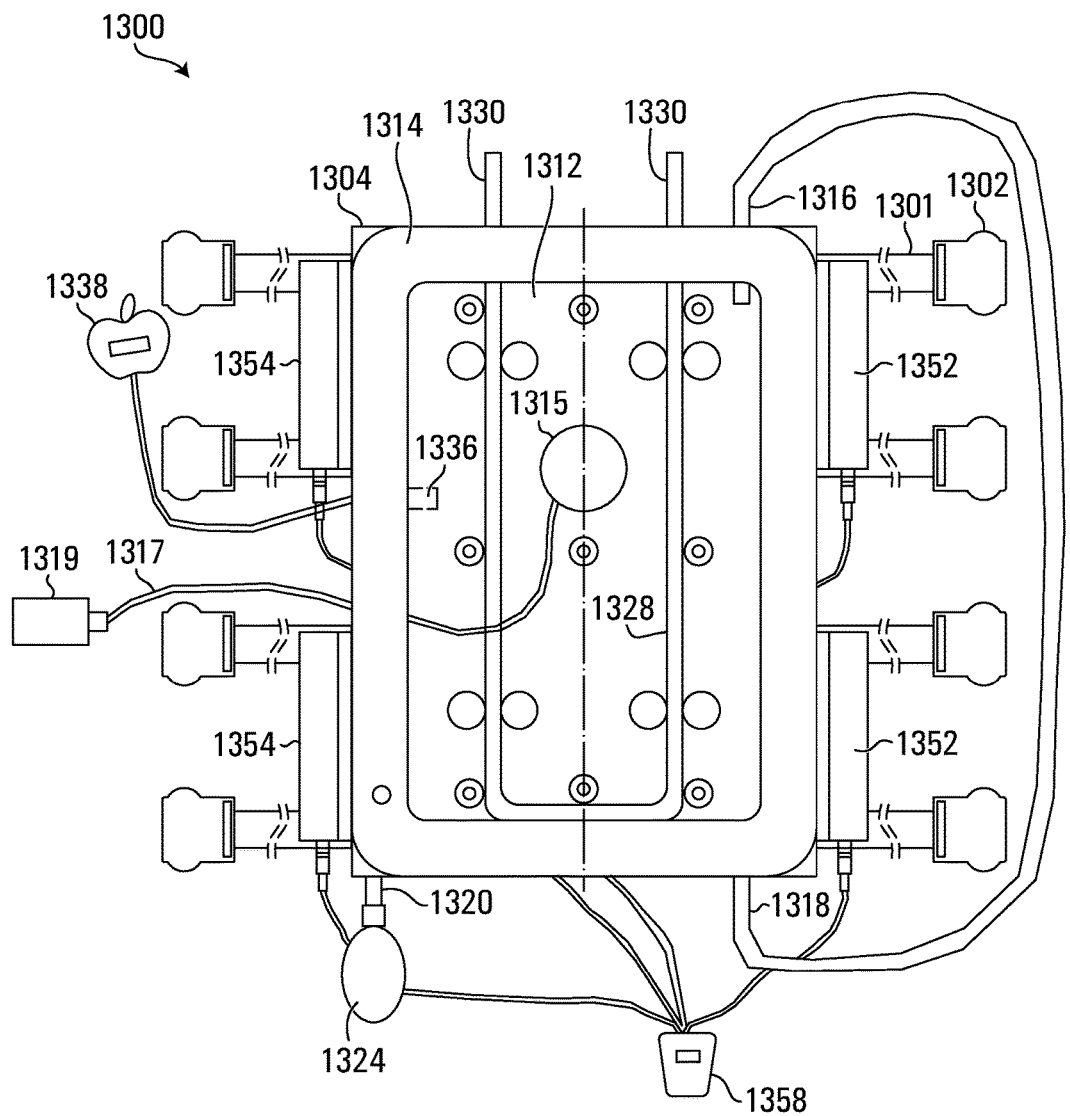
FIG. 13 is a schematic view of a different embodiment of a soaking physiotherapeutic device.

FIG. 13 illustrates another soaking and therapeutic device 1300, which has a plate-like base body 1304, similar to body 104 of device 100. Device 1300 is similar structured as device 100, in that device 1300 also has straps 1301 and buckles 1302, seals 1314 at the periphery of a tub 1312, liquid inlet/outlet tubing 1316, 1318, air conduits 1320 and air pump 1324, electrodes 1352, 1354 connected to a controller 1358, and heat-exchange fluid inlet/outlet 1330 and heat-exchange tubing 1328. In addition, Device 1300, like device 100, has a heating pad 1315 connected by wire 1317 to a heating controller 1319, and a temperature sensor 1336 connected to a temperature display 1338.

As can be appreciated, the temperature signal from sensor 1336 may be communicated by wire or wirelessly to controller 1319 for regulating the temperature in the soaking fluid in the tub 1312.

Figure 14:
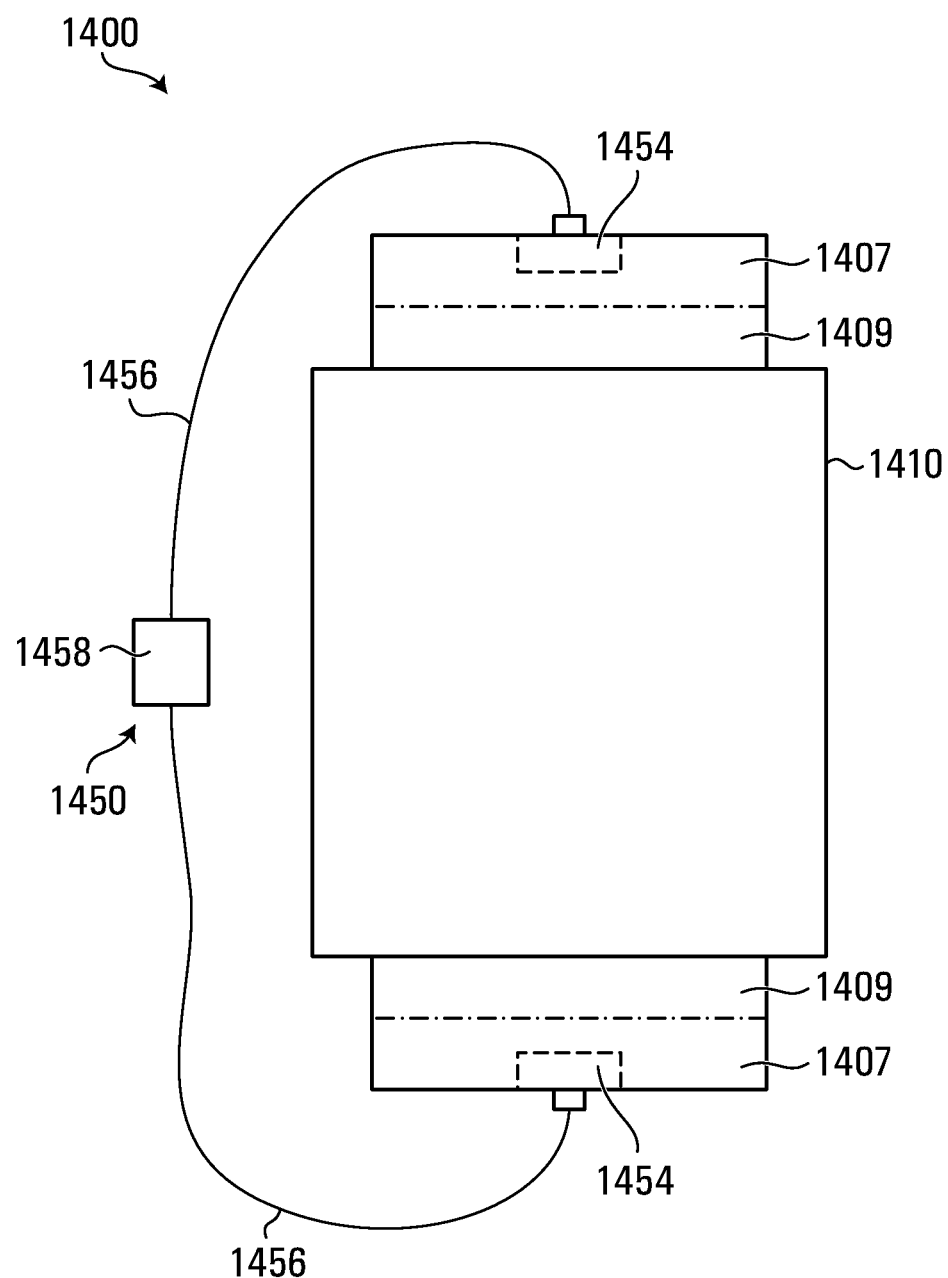
FIG. 14 is a schematic diagram for another embodiment of a soaking physiotherapeutic device.

FIG. 14 illustrate a further embodiment, device 1400 for treating a knee, which is similar to device 1100 or 1100', or 1100", except that the soaker 1410 in device 1400 has elastic tubular necks 1407 at the opposite open ends of the soaker 1410. Necks 1407 may be made of a soft and elastic material for secure device 1400 around a user's knee. For example, the necks 1407 may be made of a material similar to a material used in sports knee pads. The top neck 1407 may have a larger diameter than the lower neck 1407 since the upper leg of the user is typically thicker than the lower leg. An electrical stimulation unit 1450 may be provided, and electrode pads 1454 may be placed inside necks 1407 as illustrated. The electrode pads are connected to a controller 1458 by wires 1456. Optionally, separate straps or ropes (not shown) may be used to tighten the necks around areas marked as 1409 during use.

In different embodiments, various optional or necessary components in a particular application may be added to the therapeutic device as can be appreciated by those skilled in the art.

For example, in a particular embodiment, a large tubular soaker (not shown) may be provided to fit over a user's waist and chest.

In an embodiment, the base body of the device may include a receptacle for receiving an insert or cartridge, and the electrodes of the electrical stimulator or the entire electrical stimulator may be configured as a removable insert or cartridge that can be received in the receptacle of the base body.

As described above with reference to FIGS. 10, 10, and 12, where two or more separate inflatable seals are provided in a device, each inflatable seal may be connected to a different pressure source or to the same pressure source through separate air conduits. Each air conduit may be provided with a valve for opening and closing the conduit. Therefore, each inflatable seal may be independently inflated or deflated using the respective valve and air conduit. For example, for device 1200, the two soaking units 1210A and 1210B may be separately and independently operated.

As can be appreciated, various modifications may be made to the example devices illustrated in the drawings. For example, the different inlets and outlets, channels, tubing, and conduits may be positioned differently, and may for example pass through the back of the base body of the device instead of positioned at the sides or edges of the base body as illustrated. More or less conduits or ports may be provided in a particular device. Plugs or valves may be provided as needed for convenient closing of any fluid conduit or tubing. The shape of the base body and the entire device may also be varied depending on the part of the user body to which the device will be attached. The device may be constructed so that it is portable and may be conveniently carried by the user.

In some applications and embodiments, particularly when the soaked area is relatively small, the inflatable seals may be omitted if the straps can be used to apply sufficient pressure to keep the contact between the soaker and the skin tightly engaged to prevent liquid leaks. In such embodiments, the soaker body material and the strap material may be selected to have suitable hardness and elasticity respectively. For example, both the body and the straps may be formed of silicone materials but of different hardness and elasticity. The thickness of the material will also have an effect on the actual hardness and elasticity of the body or strap. For example, a silicone body material used for a tub body may have a thickness of 15 mm and Shore hardness (Durometer) of about 40 A. A silicone material for an inflatable seal may have a thickness of about 0.8 mm and Shore hardness of about 20 A. Straps for use with a back soaker may be formed from silicone materials with a thickness of about 2.5 mm, width of about 32 mm, and Shore hardness of about 50 A. A silicone material for the neck of a knee or elbow soaker may have a thickness of about 0.8 mm and Shore hardness of about 25 A. For use with a knee, the diameter of the bottom neck may be about 82 mm, and the diameter of the top neck may be about 100 mm, and the height of each neck may be about 75 mm. Straps for use with a knee soaker may be formed from silicone materials with a thickness of about 1.5 mm, width of about 20 mm, and Shore hardness of about 30 A. For different purposes, different grades of silicone rubber may be used. For necks and straps, the silicone material may be a high tear strength silicone rubber.

In some embodiments, an alarm system may be provided in the device, which may send out an audio or visual alarm signal when the temperature in the fluid chamber is too cold or too hot, or that the treatment time has reached a certain pre-selected threshold.

Other features, modifications, and applications of the embodiments described here may be understood by those skilled in the art in view of the disclosure herein.

CONCLUDING REMARKS

It will be understood that any range of values herein is intended to specifically include any intermediate value or sub-range within the given range, and all such intermediate values and sub-ranges are individually and specifically disclosed.

It will also be understood that the word "a" or "an" is intended to mean "one or more" or "at least one", and any singular form is intended to include plurals herein.

It will be further understood that the term "comprise", including any variation thereof, is intended to be open-ended and means "include, but not limited to," unless otherwise specifically indicated to the contrary.

When a list of items is given herein with an "or" before the last item, any one of the listed items or any suitable combination of two or more of the listed items may be selected and used.

Of course, the above described embodiments of the present disclosure are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A physiotherapeutic device attachable to a user, comprising:
    a skin soaker for soaking a portion of the user's skin with a liquid when the device is attached to the user, the soaker comprising a tub for receiving the liquid and comprising a resilient seal at a brim of the tub for sealing engagement with the skin to prevent leak of the liquid; and
    an electrical stimulator comprising a first electrode and a second electrode for contacting the skin to electrically stimulate tissues under the soaked portion of the skin, wherein the first and second electrodes are configured and positioned adjacent to the tub such that, when the soaked portion of the skin is in contact with the liquid in the tub and the first and second electrodes are in direct contact with the skin, the soaked portion of the skin extends between the first and second electrodes and the first and second electrodes are isolated from the liquid in the tub.

2. The device of claim 1, comprising a wearable body configured to be worn by the user, wherein the soaker is formed on the body and the electrical simulator is mounted on the body.

3. The device of claim 2, wherein the simulator comprises a removable insert and the body comprises a receptacle for receiving the insert.

4. The device of claim 3, further comprising a coolant tubing extending within the periphery for cooling the liquid.

5. The device of claim 3, further comprising a temperature sensor for sensing a temperature of the liquid and a controller for controlling the heater to regulate the temperature of the liquid.

6. The device of claim 2, wherein the body is configured to be worn by the user over the back, chest or belly of the user, or to be worn by the user around an elbow, a knee, or a shoulder of the user.

7. The device of claim 1, wherein the first electrode is mounted within the periphery of the soaker, and wherein the soaker comprises a sealing structure adjacent and around the first electrode for sealing engagement with the skin to isolate the first electrode.

8. The device of claim 7, wherein each one of the first and second electrodes is mounted within the periphery of the soaker.

9. The device of claim 1, wherein the soaker comprises a tub for receiving the liquid, and a fluid conduit in communication with the tub for supplying and withdrawing the fluid.

10. The device of claim 9, wherein the tub having a depth of about 2 mm to about 5 mm.

11. The device of claim 1, wherein the resilient seal comprises an inflatable seal, and the device comprises an air pump for inflating the seal, and a release valve for deflating the seal.

12. The device of claim 1, wherein the soaker is positioned between the first and second electrodes.

13. The device of claim 1, wherein the electrical stimulator is configured for neuromuscular electrical stimulation or transcutaneous electrical nerve stimulation.

14. The device of claim 1, wherein the electrical stimulator is configured for stimulating the tissues at a pulse frequency of 1 to 330 Hz.

15. The device of claim 1, further comprising a heater for heating the liquid.

16. The device of claim 1, comprising a strap for attaching the device to the user.

17. A method comprising:
    soaking a portion of a subject's skin with a treatment fluid in a tub, wherein said tub has a resilient seal for sealing engagement with the skin to prevent leakage of the treatment fluid,
    contacting a subject's skin with first and second electrodes positioned adjacent to the tub,
    wherein the electrodes are isolated from contacting the treatment fluid during the soaking and are in direct contact with the skin, and
    applying an electrical signal to the first and second electrodes to stimulate tissues under the soaked portion of the skin.

18. The method of claim 17, wherein the treatment liquid comprises a therapeutic agent.

19. The method of claim 18, wherein the treatment liquid comprises an alcohol.

20. The method of claim 17, wherein the treatment liquid is heated.

\* \* \* \* \*

UNITED STATES PATENT AND TRADEMARK OFFICE
CERTIFICATE OF CORRECTION

PATENT NO. : 10,226,623 B2
APPLICATION NO. : 15/172920
DATED : March 12, 2019
INVENTOR(S) : Jianqiao Yang Page 1 of 1

It is certified that error appears in the above-identified patent and that said Letters Patent is hereby corrected as shown below:

In the Specification

Column 2
Line 37, "electrical simulator" should read --electrical stimulator--

Column 6
Line 60, "electrical simulator" should read --electrical stimulator--

In the Claims

Claim 2
Line 3, "electrical simulator" should read --electrical stimulator--

Claim 3
Line 1, "simulator" should read --stimulator--

Signed and Sealed this
Twenty-third Day of April, 2019

Andrei Iancu
*Director of the United States Patent and Trademark Office*